United States Patent [19]

Matsuo et al.

[11] Patent Number: 5,134,142

[45] Date of Patent: Jul. 28, 1992

[54] PYRAZOLE DERIVATIVES, AND PHARMACEUTICAL COMPOSITION COMPRISING THE SAME

[75] Inventors: Masaaki Matsuo, Toyonaka; Kiyoshi Tsuji, Kishiwada; Nobukiyo Konishi, Nagaokakyo; Katsuya Nakamura, Kobe, all of Japan

[73] Assignee: Fujisawa Pharmaceutical Co., Ltd., Osaka, Japan

[21] Appl. No.: 582,358

[22] Filed: Sep. 14, 1990

[30] Foreign Application Priority Data

Sep. 22, 1989 [GB] United Kingdom ............... 8921466
Apr. 12, 1990 [GB] United Kingdom ............... 9008399

[51] Int. Cl.$^5$ ............... A61K 31/495; A61K 31/415; C07D 231/10; C07D 231/14; C07D 401/04; C07D 403/04

[52] U.S. Cl. ............... 514/255; 514/341; 514/381; 514/406; 514/407; 544/366; 546/279; 548/254; 548/374; 548/376; 548/378

[58] Field of Search ............... 548/378, 254, 374, 376; 546/279; 544/366; 514/381, 406, 407, 341, 255

[56] References Cited

U.S. PATENT DOCUMENTS

| | | | |
|---|---|---|---|
| 4,810,719 | 3/1989 | Appleton et al. | 514/406 |
| 4,826,868 | 5/1989 | Wachter et al. | 514/407 |

FOREIGN PATENT DOCUMENTS

| | | | |
|---|---|---|---|
| 1130808 | 8/1982 | Canada | 260/305.5 |
| 61-40266 | 2/1986 | Japan | 514/406 |
| 63-115867 | 5/1988 | Japan | 514/406 |
| 1-226815 | 9/1989 | Japan | 514/406 |

*Primary Examiner*—Mary C. Lee
*Assistant Examiner*—Joseph K. McKane
*Attorney, Agent, or Firm*—Oblon, Spivak, McClelland, Maier & Neustadt

[57] ABSTRACT

The present invention concerns pyrazole derivatives of formula:

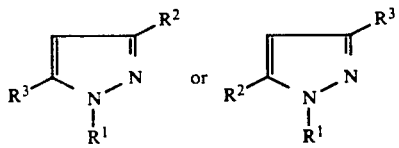

used for the treatment of inflammation, pain, thrombosis and rheumatism.

9 Claims, No Drawings

PYRAZOLE DERIVATIVES, AND PHARMACEUTICAL COMPOSITION COMPRISING THE SAME

The present invention relates to new pyrazole derivatives and pharmaceutically acceptable salts thereof.

More particularly, it relates to new pyrazole derivatives and pharmaceutically acceptable salts thereof which have antiinflammatory, analgesic and antithrombotic activities, to processes for preparation thereof, to a pharmaceutical composition comprising the same, and to methods of using the same therapeutically in the treatment and/or prevention of inflammatory conditions, various pains, collagen diseases, autoimmunediseases, various immunity diseases and thrombosis in human beings or animals, and more particularly to methods for the treatment and/or prevention of inflammation and pain in joint and muscle [e.g. rheumatoid arthritis, rheumatoid spondylitis, osteoarthritis, gouty arthritis, etc.], inflammatory skin condition [e.g. sunburn, eczema, etc.], inflammatory eye condition [e.g. conjunctivitis, etc.], lung disorder in which inflammation is involved [e.g. asthma, bronchitis, pigeon fancier's disease, farmer's lung, etc.], condition of the gastrointestinal tract associated with inflammation [e.g. aphthous ulcer, Chrohn's disease, atropic gastritis, gastritis varialoforme, ulcerative colitis, coeliac disease, regional ileitis, irritable bowel syndrome, etc.], gingivitis, inflammation, pain and tumescence after operation or injury, pyresis, pain and other conditions associated with inflammation, particularly those in which lipoxygenase and cyclooxygenase products are a factor, systemic lupus erythematosus, scleroderma, polymyositis, periarteritis nodosa, rheumatic fever, Sjögren's syndrome, Behcet disease, thyroiditis, type I diabetes, nephrotic syndrome, aplastic anemia, myasthenia gravis, uveitis contact dermatitis, psoriasis, Kawasaki disease, sarcoidosis, Hodgkin's disease, and the like. Additionally, the object compound is expected to be useful as therapeutical and/or preventive agents for cardiovascular or cerebrovascular diseases, the diseases caused by hyperglycemia and hyperlipemia.

One object of this invention is to provide new and useful pyrazole derivatives and pharmaceutically acceptable salts thereof which possess antiinflammatory, analgesic and antithrombotic activities.

Another object of this invention is to provide processes for the preparation of said pyrazole derivatives and salts thereof.

A further object of this invention is to provide a pharmaceutical composition comprising, as an active ingredient, said pyrazole derivatives and pharmaceutically acceptable salts thereof.

Still further object of this invention is to provide a therapeutical method for the treatment and/or prevention of inflammatory conditions, various pains, and the other diseases mentioned above, using said pyrazole derivatives and pharmaceutically acceptable salts thereof.

Some pyrazole derivatives having antiinflammatory and analgesic activities have been known as described, for example, in Canadian Patent 1 130 808, and EP Patent publication Nos. 272 704 and 293 220.

The object pyrazole derivatives of this invention are new and can be represented by the following general formula [I].

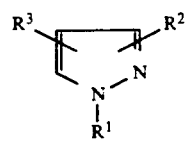

wherein
$R^1$ is aryl which may be substituted substituent(s) selected from the group consisting of lower alkyl, halogen, lower alkoxy, lower alkylthio, lower alkylsulfinyl, lower alkylsulfonyl, hydroxy, lower alkylsulfonyloxy, nitro, amino, lower alkylamino, acylamino and lower alkyl(acyl)amino; or a heterocyclic group;

$R^2$ is hydrogen; methyl substituted with amino, lower alkylamino, halogen or acyloxy; acyl; acylamino; cyano; halogen; lower alkylthio; lower alkylsulfinyl; or a heterocyclic group; and $R^3$ is aryl substituted with lower alkyl, lower alkylthio, lower alkylsulfinyl, halogen, amino, lower alkylamino, acylamino, lower alkyl(acyl)amino, lower alkoxy, cyano, hydroxy or acyl; or a heterocyclic group which may be substituted with lower alkylthio, lower alkylsulfinyl or lower alkylsulfonyl;

provided that
when $R^2$ is carboxy, esterified carboxy or tri(halo)-methyl,
then $R^3$ is aryl substituted with lower alkylthio, lower alkylsulfinyl, amino, lower alkylamino, acylamino, lower alkyl(acyl)amino, hydroxy or acyl; or a heterocyclic group substituted with lower alkylthio, lower alkylsulfinyl or lower alkylsulfonyl; or $R^1$ is aryl substituted with substituent(s) selected from the group consisting of lower alkylthio, lower alkylsulfinyl, lower alkylsulfonyl, hydroxy, lower alkylsulfonyloxy, nitro, amino, lower alkylamino, acylamino and lower alkyl(acyl)amino; or a heterocyclic group; and pharmaceutically acceptable salts thereof.

The object compound [I] or its salt can be prepared by the following processes.

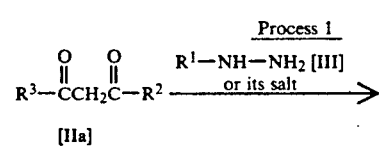

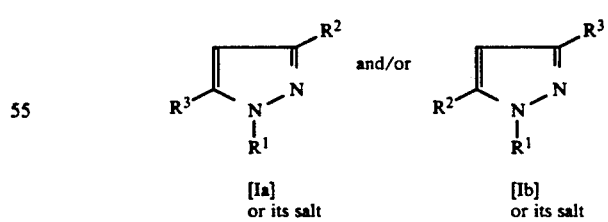

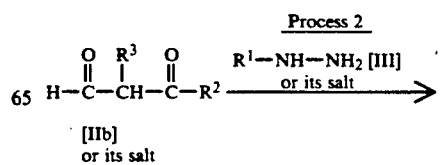

-continued
Process 2
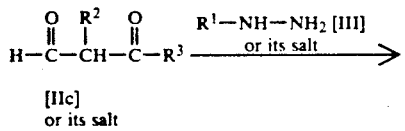
Process 7
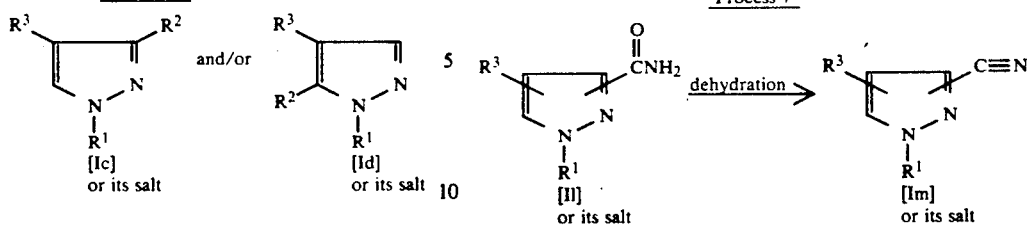
Process 3
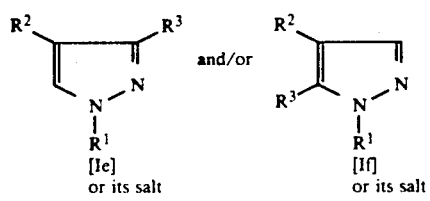
Process 8
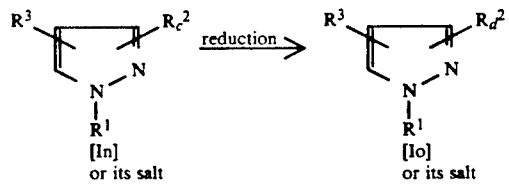
Process 4
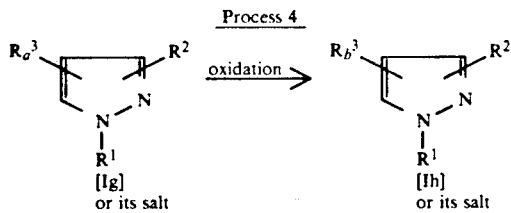
Process 9
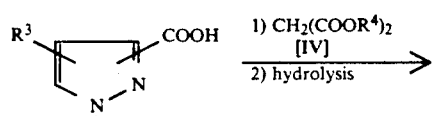
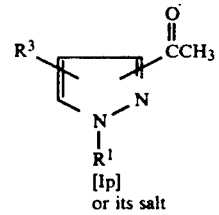
Process 5
Process 10
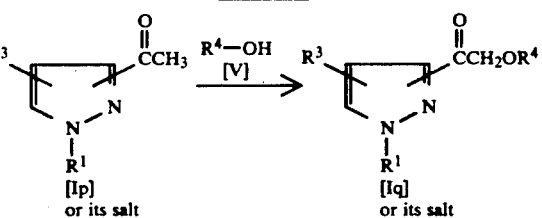
Process 6
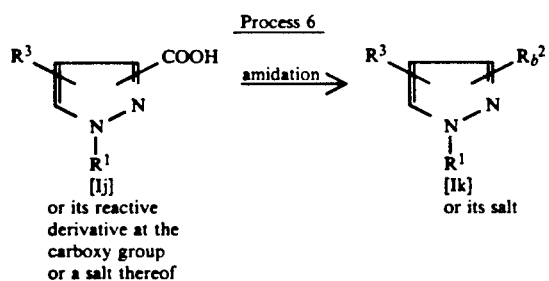
Process 11
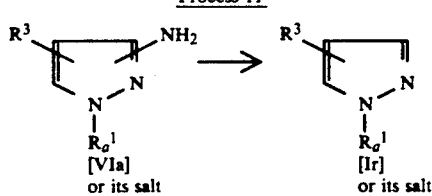

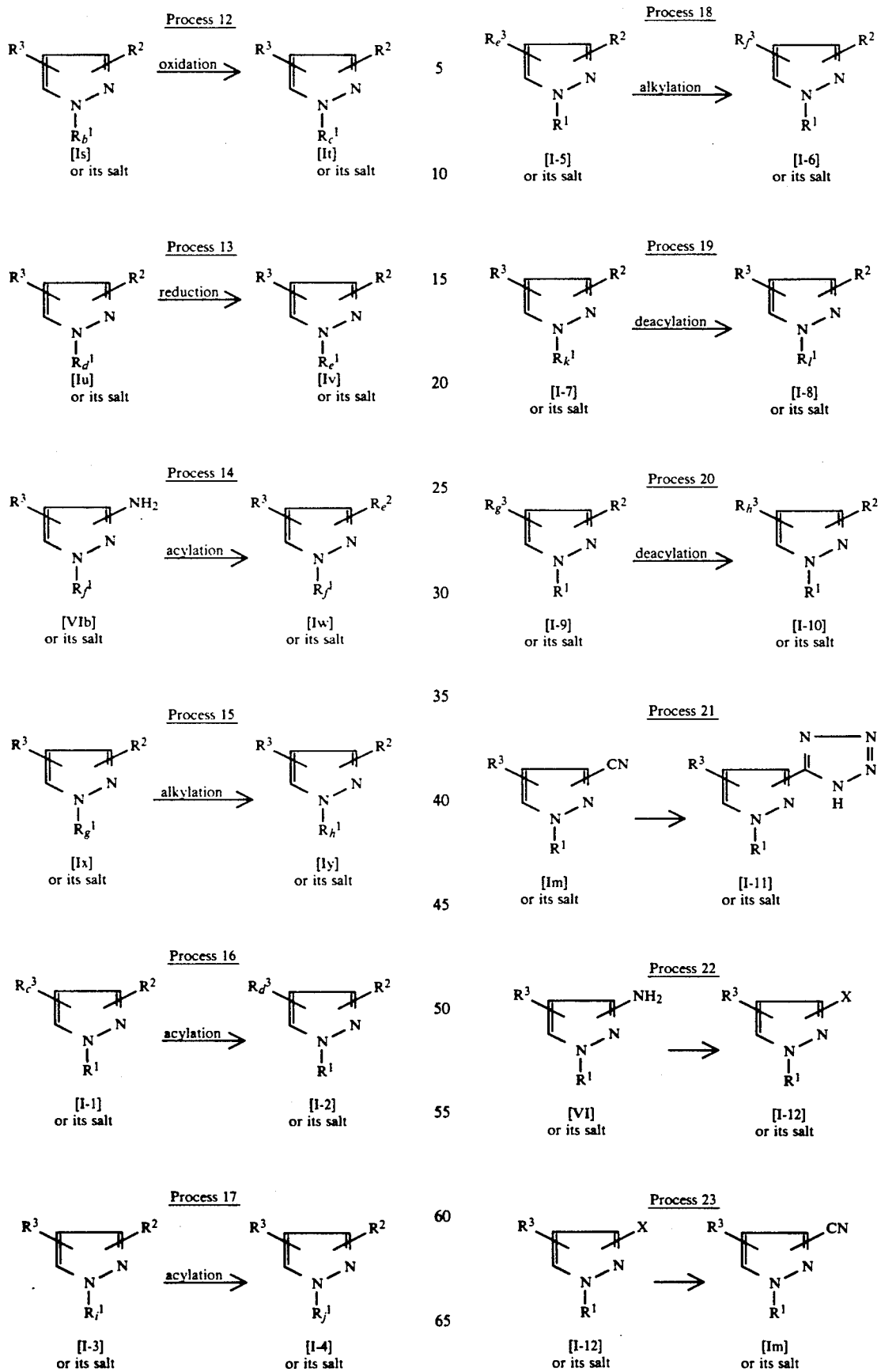

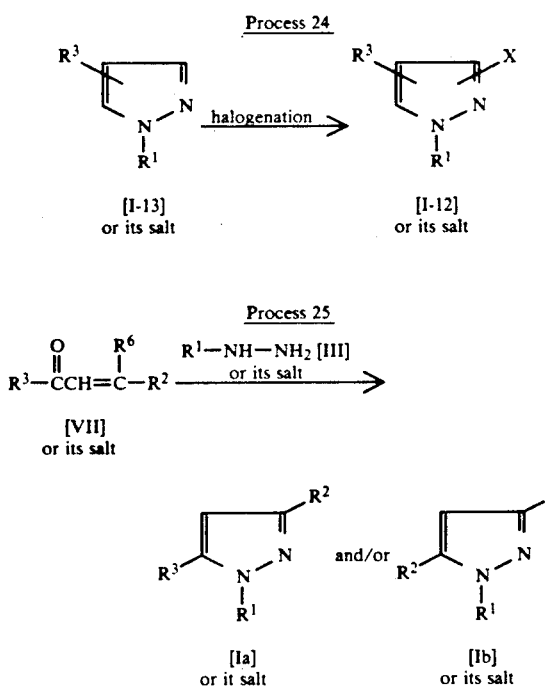

Process 24

[I-13] or its salt → halogenation → [I-12] or its salt

Process 25

[VII] or its salt + $R^1$—NH—NH$_2$ [III] or its salt → [Ia] or its salt and/or [Ib] or its salt wherein $R^1$, $R^2$ and $R^3$ are each as defined above, $R_a^3$ is aryl or a heterocyclic group, each of which is substituted with lower alkylthio, $R_b^3$ is aryl or a heterocyclic group, each of which is substituted with lower alkylsulfinyl or lower alkylsulfonyl, $R_a^2$ is esterified carboxy, $R_b^2$ is carbamoyl which may be substituted with substituent(s) selected from the group consisting of lower alkyl, aryl, cyclo(lower)alkyl and hydroxy; or N-containing heterocycliccarbonyl;

$R_c^2$ is carbamoyl which may be substituted with lower alkyl, $R_d^2$ is aminomethyl which may be substituted with lower alkyl, $R^4$ is lower alkyl, $R_a^1$ is aryl which may be substituted with substituent(s) selected from the group consisting of lower alkyl, halogen, lower alkoxy, lower alkylthio, lower alkylsulfinyl, lower alkylsulfonyl, hydroxy, lower alkylsulfonyloxy, nitro, lower alkylamino, acylamino and lower alkyl(acyl)amino; or a heterocyclic group;

$R_b^1$ is aryl substituted with lower alkylthio, $R_c^1$ is aryl substituted with lower alkylsulfinyl or lower alkylsulfonyl, $R_d^1$ is aryl substituted with nitro, $R_e^1$ is aryl substituted with amino, $R_f^1$ is aryl which may be substituted with substituent(s) selected from the group consisting of lower alkyl, halogen, lower alkoxy, lower alkylthio, lower alkylsulfinyl, lower alkylsulfonyl, lower alkylsulfonyloxy, nitro, acylamino and lower alkyl(acyl)amino; or a heterocyclic group, $R_e^2$ is acylamino, $R_g^1$ is aryl substituted with amino or acylamino, $R_h^1$ is aryl substituted with lower alkylamino or lower alkyl(acyl)amino, $R_c^3$ is aryl substituted with amino, $R_d^3$ is aryl substituted with acylamino, $R_i^1$ is aryl substituted with amino, $R_j^1$ is aryl substituted with acylamino, $R_e^3$ is aryl substituted with amino or acylamino, $R_f^3$ is aryl substituted with lower alkylamino or lower alkyl(acyl)amino, $R_k^1$ is aryl substituted with acylamino or lower alkyl(acyl)amino, $R_l^1$ is aryl substituted with amino or lower alkylamino, $R_g^3$ is aryl substituted with acylamino or lower alkyl(acyl)amino, $R_h^3$ is aryl substituted with amino or lower alkylamino, X is halogen, and $R^6$ is lower alkylthio.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" and lower alkyl moiety in the terms "lower alkylthio", "lower alkylsulfonyl", "lower alkyl(acyl)amino", "lower alkylsulfinyl" and "lower alkylsulfonyloxy" may be a straight or branched one such as methyl, ethyl, propyl, isopropyl, butyl, isobutyl, tert-butyl, pentyl, hexyl or the like, in which preferable one is methyl.

Suitable "lower alkoxy" may be methoxy, ethoxy, propoxy, isopropoxy, butoxy, isobutoxy, tert-butoxy and the like, in which preferable one is methoxy.

Suitable "aryl" may be phenyl, naphthyl, and the like, in which preferable one is phenyl.

The aryl group for $R^1$ may be substituted with 1 to 5 substituent(s) as mentioned above and the aryl group for $R^3$ is substituted with 1 to 5 substituent(s) as stated above, wherein the preferable number of the substituent(s) is 1 to 3.

Suitable "heterocyclic group" may include saturated or unsaturated, monocyclic or polycyclic one containing at least one hetero atom such as nitrogen atom, oxygen atom or sulfur atom.

The preferred examples of thus defined "heterocyclic group" may be unsaturated, 3 to 8-membered, more preferably 5 or 6-membered heteromonocyclic group containing 1 to 4-nitrogen atom(s), for example, pyrrolyl, imidazolyl, pyrazolyl, pyridyl, pyridyl N-oxide, dihydropyridyl, tetrahydropyridyl, pyrimidyl, pyrazinyl, pyridazinyl, triazinyl, triazolyl, tetrazinyl, tetrazolyl, etc.;

saturated, 3 to 8-membered, more preferably 5 or 6-membered heteromonocyclic group containing 1 to 4 nitrogen atom(s), for example, pyrrolidinyl, imidazolidinyl, piperidino, piperazinyl, etc.;

unsaturated, condensed heterocyclic group containing 1 to 5 nitrogen atom(s), for example, indolyl, isoindolyl, indolizinyl, benzimidazolyl, quinolyl, isoquinolyl, indazolyl, benzotriazolyl, etc.;

unsaturated, 3 to 8-membered heteromonocyclic group containing 1 to 2 oxygen atom(s) and 1 to 3 nitrogen atom(s), for example, oxazolyl, isoxazolyl, oxadiazolyl, etc.;

saturated, 3 to 8-membered heteromonocyclic group containing 1 to 2 oxygen atom(s) and 1 to 3 nitrogen atom(s), for example, morpholino, sydnonyl, etc.;

unsaturated, condensed heterocyclic group containing 1 to 2 oxygen atom(s) and 1 to 3 nitrogen atom(s), for example, benzoxazolyl, benzoxadiazolyl, etc.;

unsaturated, 3 to 8-membered heteromonocyclic group containing 1 to 2 sulfur atom(s) and 1 to 3 nitrogen atom(s), for example, thiazolyl, isothiazolyl, thiadiazolyl, etc.;

unsaturated, 3 to 8-membered heteromonocyclic group containing 1 to 2 sulfur atom(s), for example, thienyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated, 3 to 8-membered heteromonocyclic group containing an oxygen atom, for example, furyl, etc.;

unsaturated, condensed heterocyclic group containing 1 to 2 sulfur atom(s), for example, benzothienyl, etc.;

unsaturated, condensed heterocyclic group containing 1 to 2 oxygen atom(s), for example, benzofuranyl, etc.; or the like.

Said "heterocyclic group" may be substituted with lower alkyl as exemplified above, in which preferable one is pyrrolidinyl, N-methylpiperazinyl, tetrazolyl, thienyl or pyridyl.

Suitable "cyclo(lower)alkyl" may be cyclopropyl, cyclobutyl, cyclopentyl, cyclohexyl and the like, in which preferable one is cyclopropyl.

Suitable "halogen" may be fluorine, chlorine, bromine and iodine, in which preferable one is fluorine.

Suitable "lower alkylamino(lower)alkyl" may be mono or di(lower alkyl)amino substituted lower alkyl such as methylaminomethyl, methylaminoethyl, methylaminopropyl, methylaminohexyl, ethylaminomethyl, ethylaminoethyl, ethylaminopropyl, ethylaminohexyl, dimethylaminomethyl, dimethylaminoethyl, dimethylaminopropyl, dimethylaminohexyl, diethylaminomethyl, diethylaminoethyl, diethylaminopropyl, diethylaminohexyl or the like.

Suitable "lower alkylamino" and lower alkylamino moiety in the term "lower alkylaminomethyl" may be mono or di(lower)alkylamino such as methylamino, ethylamino, dimethylamino, diethylamino or the like.

Suitable "halo(lower)alkyl" may be chloromethyl, fluoromethyl, bromomethyl, difluoromethyl, dichloromethyl, trifluoromethyl, trichloromethyl, 2-fluoroethyl and the like.

Suitable "acyl" and acyl moiety in the terms "acyloxy", "acylamino" and "lower alkyl(acyl)amino" may be carboxy; esterified carboxy; carbamoyl optionally substituted with substituent(s) selected from the group consisting of lower alkyl, cyclo(lower)alkyl, aryl and hydroxy; lower alkanoyl optionally substituted with lower alkoxy; a heterocycliccarbonyl; lower alkylsulfonyl; and the like.

The esterified carboxy may be substituted or unsubstituted lower alkoxycarbonyl [e.g. methoxycarbonyl, ethoxycarbonyl, propoxycarbonyl, butoxycarbonyl, hexyloxycarbonyl, 2-iodoethoxycarbonyl, 2,2,2-trichloroethoxycarbonyl, etc.], substituted or unsubstituted aryloxycarbonyl [e.g. phenoxycarbonyl, 4-nitrophenoxycarbonyl, 2-naphthyloxycarbonyl, etc.], substituted or unsubstituted ar(lower)alkoxycarbonyl [e.g. benzyloxycarbonyl, phenethyloxycarbonyl, benzhydryloxycarbonyl, 4-nitrobenzyloxycarbonyl, etc.] and the like.

The lower alkanoyl may be formyl, acetyl, propionyl, butyryl, isobutyryl, valeryl, isovaleryl, pivaloyl, hexanoyl and the like.

The heterocyclic moiety in the term "heterocycliccarbonyl" may be the same as those exemplified for "heterocyclic group".

Suitable "heterocycliccarbonyl" may be N-containing heterocycliccarbonyl such as pyrrolidinylcarbonyl, imidazolidinylcarbonyl, piperidinocarbonyl, piperazinylcarbonyl, N-methylpiperazinylcarbonyl or the like, in which preferable one is pyrrolidinylcarbonyl or N-methylpiperazinylcarbonyl.

Suitable "lower alkylsulfonyl" may be methylsulfonyl, ethylsulfonyl, propylsulfonyl and the like, in which preferable one is methylsulfonyl.

Suitable "lower alkylsulfinyl" may be methylsulfinyl, ethylsulfinyl, propylsulfinyl and the like, in which preferable one is methylsulfinyl.

Suitable pharmaceutically acceptable salts of the object compound [I] are conventional non-toxic salts and include acid addition salt such as an inorganic acid addition salt [e.g. hydrochloride, hydrobromide, sulfate, phosphate, etc.], an organic acid addition salt [e.g. formate, acetate, trifluoroacetate, maleate, tartrate, methanesulfonate, benzenesulfonate, toluenesulfonate, etc.], a salt with an amino acid [e.g. arginine salt, aspartic acid salt, glutamic acid salt, etc.], a metal salt such as an alkali metal salt [e.g. sodium salt, potassium salt, etc.]and an alkaline earth metal salt [e.g. calcium salt, magnesium salt, etc.], an ammonium salt, an organic base addition salt [e.g. trimethylamine salt, triethylamine salt, etc.] and the like.

The processes for preparing the object compound [I] are explained in detail in the following.

PROCESS 1

The compound [Ia] or its salt and/or the compound [Ib] or its salt can be prepared by reacting a compound [IIa] or its salt with a compound [III] or its salt.

Suitable salts of the compound [IIa] and [III] may be the same as those exemplified for the compound [I].

This reaction is usually carried out in a conventional solvent such as alcohol (e.g. methanol, ethanol, etc.), dioxane, tetrahydrofuran, acetic acid or any other organic solvent which does not adversely influence the reaction.

The reaction temperature is not critical, and the reaction is usually carried out under heating.

PROCESS 2

The compound [Ic] or its salt and/or the compound [Id] or its salt can be prepared by reacting a compound [IIb] or its salt with a compound [III] or its salt.

Suitable salts of the compound [IIb] and [III] may be the same as those exemplified for the compound [I].

This reaction can be carried out in substantially the same manner as Process 1, and therefore the reaction mode and reaction condition (e.g. solvent, reaction temperature, etc.) of this reaction are to be referred to those as explained in Process 1.

PROCESS 3

The compound [Ie] or its salt and/or the compound [If] or its salt can be prepared by reacting a compound [IIc] or its salt with a compound [III] or its salt.

Suitable salts of the compound [IIc] and [III] may be the same as those exemplified for the compound [I].

This reaction can be carried out in substantially the same manner as Process 1, and therefore the reaction mode and reaction condition (e.g. solvent, reaction temperature, etc.) of this reaction are to be referred to those as explained in Process 1.

PROCESS 4

The compound [Ih] or its salt can be prepared by reacting a compound [Ig] or its salt with an oxidizing agent.

The suitable oxidizing agent may be hydrogen peroxide, Jones reagent, peracid [e.g. peracetid acid, perbenzoic acid, m-chloroperbenzoic acid, etc.], chromic acid, potassium permanganate, alkali metal periodate [e.g. sodium periodate, etc.] and the like.

This reaction is usually carried out in a solvent which does not advaersely influence the reaction such as acetic acid, dichloromethane, acetone, ethyl acetate, chloroform, water, an alcohol [e.g. methanol, ethanol, etc.], a mixture thereof or the like.

The reaction temperature is not critical, and the reaction is usually carried out under cooling to warming.

In this reaction, in case that the compound [Ig] having aryl substituted with lower alkylthio for $R^1$ and/or lower alkylthio for $R^2$ is used as a starting compound, the compound [Ih] having aryl substituted with lower alkylsulfinyl or lower alkylsulfonyl for $R^1$ and/or lower alkylsulfinyl or lower alkylsulfonyl for $R^2$ may be obtained according to reaction conditions. These cases are included within the scope of the present reaction.

PROCESS 5

The compound [Ij] and its salt can be prepared by subjecting a compound [Ii] or its salt to deesterification reaction.

The reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4,3,0]non-5-ene, 1,4-diazabicyclo[2,2,2]octane, 1,8-diazabicyclo[5,4,0]undec-7-ene, or the like. Suitable acid may include an organic acid [e.g. formic acid, acetic acid, propionic acid, trichloroacetic acid, trifluoroacetic acid, etc.], an inorganic acid [e.g. hydrochloric acid, hyirobromic acid, hydroiodic acid, sulfuric acid, etc.] and Lewis acid [e.g. boron tribromide, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reaction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, aoetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reduction is usually carried out in a conventional solvent which does not adversely influence the reaction such as water, an alcohol [e.g. methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

In the present reaction, when the compound [Ii] having aryl substituted with lower alkoxy for $R^1$ is used as a starting compound, the compound [Ij] having aryl substituted with hydroxy for $R^1$ may be obtained according to reaction conditions. This case is also included within the scope of the present reaction.

PROCESS 6

The compound [Ik] or its salt can be prepared by reacting a compound [Ij] or its reactive derivative at the carboxy group or a salt thereof with an amine, or formamide and alkali metal alkoxide.

Suitable "amine" may be ammonia, lower alkylamine, arylamine, cyclo(lower)alkylamine, lower alkylhydroxylamine, an amino acid, N-containing heterocyclic compound and the like.

The lower alkylamine may be mono or di(lower)-alkylamine such as methylamine, ethylamine, propylamine, isopropylamine, butylamine, isobutylamine, pentylamine, hexylamine, dimethylamine, diethylamine, dipropylamine, dibutylamine, di-isopropylamine, dipentylamine, dihexylamine or the like, in which preferable one is methylamine or dimethylamine.

The arylamine may be aniline, naphthylamine and the like. The cyclo(lower)alkylamine may be cyclopropylamine, cyclobutylamine cyclopentylamine, cyclohexylamine and the like, in which preferable one is cyclopropylamine.

The lower alkylhydroxylamine may be methylhydroxylamine, ethylhydroxylamine, propylhydroxylamine, butylhydroxylamine, isopropylhydroxylamine and the like, in which preferable one is methylhydroxylamine.

The amino acid may be glycine, alanine, $\beta$-alanine, isoleucine, tyrosine and the like, in which preferable one is glycine.

The N-containing heterocyclic compound may be saturated 5 or 6-membered N-, or N- and S-, or N- and O-containing heterocyclic compound such as pyrrolidine, imidazolidine, piperidine, piperazine, N-(lower)alkylpiperazine e.g. N-methylpiperazine, N-ethylpiperazine, etc.], morpholine, thiomorpholine or the like, in which preferable one is pyrrolidine or N-methylpiperazine.

Suitable "alkali metal alkoxide" may be sodium methoxide, sodium ethoxide, potassium tert-butoxide and the like.

Suitable reactive derivative at the carboxy group of the compound [Ij] may include an ester, an acid halide, an acid anhydride and the like. The suitable examples of the reactive derivatives may be an acid halide [e.g. acid chloride, acid bromide, etc.]; a symmetrical acid anhydride; a mixed acid anhydride with 1,1'-carbonyl diimidazole or an acid such as aliphatic acid [e.g. acetic acid, pivalic acid, etc., substituted phosphoric acid [e.g. dialkylphosphoric acid, diphenylphosphoric acid, etc.]; an ester such as lower alkyl ester [e.g. methyl ester, ethyl ester, propyl ester, hexyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxy-6-chloro-1H-benzotriazole, or the like.

The reaction is usually carried out in a conventional solvent such as water, acetone, dioxane, chloroform, methylene chloride, ethylene chloride, tetrahydrofuran, formamide, ethyl acetate, N,N-dimethylformamide, pyridine or any other organic solvent which does not adversely influence the reaction. Among these solvents, hydrophilic solvents may be used in a mixture with water.

When the compound [Ij] is used in a free acid form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like. The reaction is also preferable carried out in the presence of a conventional base such as triethylamine, pyridine, sodium hydroxide or the like.

The reaction temperature is not critical, and the reaction can be carried out under cooling to heating.

PROCESS 7

The compound [Im] or its salt can be prepared by reacting a compound [Il] or its salt with a dehydrating agent.

Suitable dehydrating agent may be phosphorus compound [e.g. phosphorus pentoxide, phosphorus pentachloride, phosphorus oxychloride, etc.], thionyl chloride, acid anhydride [e.g. acetic anhydride, etc.], phosgene, arylsulphonyl chloride [e.g. benzenesulfonyl chloride, p-toluenesulfonyl chloride, etc.], methanesulfonyl chloride, sulfamic acid, ammonium sulfamate, N,N'-dicyclohexylcarbodiimide, lower alkoxycarbonyl halide [e.g. ethyl chloroformate, etc.] and the like.

The reaction is usually carried out in a conventional solvent such as acetonitrile, methylene chloride, ethylene chloride, benzene, N,N-dimethylformamide, pyridine or any other organic solvent which does not adversely influence the reaction.

Additionally in case that the above-mentioned dehydrating agents are in liquid, they can also be used as a solvent.

The reaction temperature is not critical and the reaction is preferably carried out under warming or heating.

In the present reaction, when methylsulfonyl chloride as a dehydrating agent and the compound [Il] having aryl substituted with hydroxy for $R^1$ and/or aryl substituted with amino for $R^3$ as a starting compound are used, the compound [Im] having aryl substituted with methylsulfonyloxy for $R^1$ and/or aryl substituted with methylsulfonylamino for $R^3$ may be obtained according to reaction conditions. These cases are also included within the scope of the present reaction.

PROCESS 8

The compound [Io] or its salt can be prepared by reacting a compound [In] or its salt with a reducing agent.

Suitable reducing agent may be diborane, lithium aluminum hydride and the like.

The reaction is usually carried out in a conventional solvent such as diethyl ether, tetrahydrofuran or any other organic solvent which does not adversely influence the reaction.

The reaction temperature is not critical, and the reaction can be carried out under cooling to heating.

PROCESS 9

The compound [Ip] can be prepared by the following methods.

Namely, (1) the compound [Ij] or its reactive derivative at the carboxy group or a salt thereof is firstly reacted with a compound [IV], and then (2) subjecting the resultant product to hydrolysis reaction.

Suitable reactive derivative at the carboxy group of the compound [Ij] may be an acid halide [e.g. acid chloride, acid bromide, etc.], and the like.

In the first step, the reaction is preferably carried out in the presence of a base such as an alkali metal [e.g. lithium, sodium, potassium, etc.], alkaline earth metal [e.g. calcium, magnesium, etc.], alkali metal hydride [e.g. sodium hydride, etc.], alkaline earth metal hydride [e.g. calcium hydride, etc.], alkali metal alkoxide [e.g. sodium methoxide, sodium ethoxide, potassium tert-butoxide, etc.], alkaline earth metal alkoxide [e.g. magnesium methoxide, magnesium ethoxide, etc.] and the like.

The reaction is usually carried out in a solvent which does not adversely influence the reaction such as diethyl ether, tetrahydrofuran, dioxane and the like.

The reaction temperature is not critical and the reaction can be carried out under cooling to heating.

In this reaction, a compound of the formula :

$$R^3-\underset{\underset{R^1}{|}}{\underset{N-N}{\boxed{\phantom{xx}}}}-CCH(CO_2R^4)_2 \quad [Iz]$$

or its salt wherein $R^1$, $R^3$ and $R^4$ are each as defined above, may be obtained.

The compound [Iz] or its salt is further subjected to hydrolysis to give the compound [Ip] or its salt.

The hydrolysis is preferably carried out in the presence of an acid.

Suitable acid may be the same as those exemplified in the above-mentioned Process 5.

This hydrolysis reaction mode and reaction conditions can be referred to those as explained in the above-mentioned Process 5.

PROCESS 10

The compound [Iq] or its salt can be prepared by reacting a compound [Ip] or its salt with a compound [V].

The present reaction is preferably carried out in the presence of a thallium(III) salt [e.g. thallium(III) nitrate, etc.] and the like.

The reaction is usually carried out in a solvent such as dioxane, tetrahydrofuran or any other organic solvent which does not adversely influence the reaction.

The reaction temperature is not critical and the reaction is preferably carried out at ambient temperature or under warming to heating.

PROCESS 11

The compound [Ir] or its salt can be prepared by reacting a compound [VIa] or its salt with a nitrate compound.

Suitable salt of the compound [VIa] may be the same as those exemplified for the compound [I].

Suitable nitrite compound may be alkali metal nitride [e.g. sodium nitrite, potassium nitrite, etc.], alkyl nitrite [e.g. tert-butyl nitrite, etc.] and the like.

The present reaction is usually carried out in the presence of cupric chloride, hypophosphorous acid and the like.

The reaction is usually carried out in a solvent such as dioxane, tetrahydrofuran, acetonitrile or any other organic solvent which does not adversely influence the reaction.

The reaction temperature is not critical and the reaction can be carried out under cooling to heating.

PROCESS 12

The compound [It] or its salt can be prepared by reacting a compound [Is] or its salt with an oxidizing agent.

This reaction can be carried out in substantially the same manner as that of Process 4, and therefore the reaction mode and reaction conditions (e.g. solvent, reaction temperature, etc.) of this reaction are to be referred to those as explained in Process 4.

In this reaction, in case that the compound [Is] having lower alkylthio for $R^2$ and/or aryl or a heterocyclic group, each of which is substituted with lower alkylthio for $R^3$, is used as a starting compound, the compound [It] having lower alkylsulfinyl or lower alkylsulfonyl for $R^2$ and/or aryl or a heterocyclic group, each of which is substituted with lower alkylsulfinyl or lower alkylsulfonyl for $R^3$ may be obtained according to reaction conditions. These cases are included within the scope of the present reaction.

PROCESS 13

The compound [Iv] or its salt can be prepared by reducing the compound [Iu] or its salt.

The reaction may include chemical reduction and catalytic reduction, which are carried out in a conventional manner.

Suitable reducing agents to be used in chemical reduction are a metal [e.g. tin, zinc, iron, etc.], a combination of such metal and/or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], a combination of such metal and/or metallic compound and base [e.g. ammonia, ammonium chloride, sodium hydroxide, etc.], a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, bonane, diborane, etc.], a phosphorus compound [e.g. phosphorus trichloride, phosphorus tribromide, triphenylphosphine, triethylphosphine, etc.] an the like.

Suitable catalysts to be used in catalytic reduction are conventional ones such as platinum catalyst [e.g. platinum plate, spongy platinum, platinum black, colloidal platinum, platinum oxide, platinum wire, etc. , palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The reduction is usually carried out in a solvent. A suitable solvent to be used may be water, an alcohol [e.g. methanol, ethanol, propanol, etc.], acetonitrile or any other conventional organic solvent such as diethyl ether, dioxane, tetrahydrofuran, etc. or a mixture thereof.

The reaction temperature is not critical, and the reaction is preferably carried out under warming to heating.

PROCESS 14

The compound [Iw] can be prepared by reacting a compound [VIb] or its salt with an acylating agent.

Suitable salt of the compound [VIb] may be the same as those exemplified for the compound [I].

The acylating agent may include an organic acid represented by the formula : $R^5$—OH, in which $R^5$ is acyl as Illustrated above, or its reactive derivative.

The suitable reactive derivative of organic acid may be a conventional one such as an acid halide [e.g. acid chloride, acid bromide, etc.], an acid azide, an acid anhydride, an activated amide, an activated ester or the like.

When free acid is used as an acylating agent, the acylation reaction may preferably be conducted in the presence of a conventional condensing agent such as N,N'-dicyclohexylcarbodiimide or the like.

The reaction is usually carried out in a conventional solvent such as water, acetone, dioxane, chloroform, methylene chloride, acetonitrile, ethylene chloride, tetrahydrofuran, ethyl acetate, N,N-dimethylformamide, pyridine or any other organic solvent which does not adversely influence the reaction, or a mixture thereof.

The reaction is also preferably carried out in the presence of a conventional base such as triethylamine, pyridine, sodium hydroxide or the like.

The reaction temperature is not critical, and the reaction can be carried out under cooling to heating.

PROCESS 15

The compound [Iy] or its salt can be prepared by reacting a compound [Ix] or its salt with an alkylating agent.

Suitable alkylating agent may be lower alkyl halide [e.g. methyl iodide, ethyl bromide, etc.], a combination of a carbonyl compound such as aliphatic ketone [e.g. acetone, ethyl methyl ketone, etc.], carbaldehyde [e.g. formaldehyde, ethanal, etc.]orthocarboxylic acid ester [e.g. triethyl orthoformate, etc.] or the like, and a reducing agent including chemical and catalytic ones [e.g. formic acid, sodium borohydride, sodium cyanoborohydride, palladium on carbon, etc.].

When lower alkyl halide is used as alkylating agent, the reaction is preferably carried out in the presence of a base such as an alkali metal [e.g. sodium, potassium, etc.], an alkaline earth metal [e.g. magnesium, calcium, etc.], the hydride or hydroxide or carbonate or bicarbonate thereof.

The reaction is usually carried out in a conventional solvent which does not adversely influence the reaction such as water, dioxane, an alcohol [e.g. methanol, ethanol, etc.], acetonitrile, tetrahydrofuran, N,N-dimethylformamide, or a mixture thereof. Additionally, in case that the above-mentioned alkylating agent are in liquid, they can also be used as a solvent.

The reaction temperature is not critical and the reaction can be carried out under cooling to heating.

In this reaction, in case that the compound [Ix] having aminomethyl for $R^2$ and/or aryl substituted with amino or acylamino for $R^3$ is used as a starting compound, the compound [Iy] having lower alkylaminomethyl for $R^2$ and/or aryl substituted with lower alkylamino or lower alkyl(acyl)amino for $R^3$ may be obtained according to reaction conditions. These cases are included within the scope of the present reaction.

PROCESS 16

The compound [I-2] or its salt can be prepared by reacting a compound [I-1] or its salt with acylating agent.

This reaction can be carried out in substantially the same manner as that of Process 14, and therefore the reaction mode and reaction conditions (e.g. solvent, reaction temperature, etc.) of this reaction are to be referred to those a explained in Process 14.

In this reaction, in case that the compound [I-1] having aryl substituted with amino or hydroxy for $R^1$ and/or aminomethyl for $R^2$ is used as a starting compound, the compound [I-2] having aryl substituted with acylamino or acyloxy for $R^1$ and/or acylaminomethyl for $R^2$ may be obtained according to reaction conditions. These cases are included within the scope of the present reaction.

PROCESS 17

The compound [I-4] or its salt can be prepared by reacting a compound [I-3] or its salt with acylating agent.

This reaction can be carried out in substantially the same manner as that of Process 14, and therefore the reaction mode and reaction conditions (e.g. solvent, reaction temperature, etc. of this reaction are to be referred to those as explained in Process 14.

In this reaction, in case that the compound [I-3] having aryl substituted with amino or hydroxy for $R^3$ and/or aminomethyl for $R^2$ is used as a starting compound, the compound [I-4] having aryl substituted with acylamino or acyloxy for $R^3$ and/or acylaminomethyl for $R^2$ may be obtained according to reaction conditions. These cases are included within the scope of the present reaction.

PROCESS 18

The compound [I-6] or its salt can be prepared by reacting a compound [I-5] or its salt with an alkylating agent.

This reaction can be carried out in substantially the same manner as that of Process 15, and therefore the reaction mode and reaction conditions (e.g. solvent, reaction temperature, etc.) of this reaction are to be referred to those as explained in Process 15.

In this reaction, in case that the compound [I-5] having aminomethyl for $R^2$ and/or aryl substituted with amino or acylamino for $R^1$ is used as a starting compound, the compound [I-6] having lower alkylaminomethyl for $R^2$ and/or aryl substituted with lower alkylamino or lower alkyl(acyl)amino for $R^1$ may be obtained according to reaction conditions. These cases are included within the scope of the present reaction.

PROCESS 19

The compound [I-8] or its salt can be prepared by subjecting a compound [I-7] or its salt to deacylation reaction.

This reaction may preferably be conduced in the presence of an inorganic acid [e.g. hydrochloric acid, hydrobromic acid, etc.]and an organic acid [e.g. trifluoroacetic acid, methanesulfonic acid, toluenesulfonic acid, etc.].

The reaction is usually carried out in a conventional solvent such as water, an alcohol [e.g. methanol, ethanol, etc.], tetrahydrofuran, dioxane or any other organic solvent which does not adversely influence the reaction, or a mixture thereof.

The reaction temperature is not critical, and the reaction can be carried out cooling to heating.

In this reaction, in case that the compound [I-7] having aryl substituted with acylamino or lower alkyl(acyl)amino for $R^3$ is used as a starting compound, the compound [I-8] having aryl substituted with amino or lower alkylamino for $R^3$ may be obtained according to reaction conditions. This case is included within the scope of the present reaction.

PROCESS 20

The compound [I-10] or its salt can be prepared by subjecting a compound [I-9] or its salt to deacylation reaction.

This reaction can be carried out in substantially the same manner as that of Process 19, and therefore the reaction mode and reaction conditions (e.g. solvent, reaction temperature, etc.) of the reaction are to be referred to those as explained in Process 19.

In this reaction, in case that the compound [I-9] having aryl substituted with acylamino or lower alkyl(acyl)amino for $R^1$ is used as a starting compound, the compound [I-10] having substituted with amino or lower alkylamino for $R^1$ may be obtained according to reaction conditions. This case is included within the scope of the present reaction.

PROCESS 21

The compound [I-11] or its salt can be prepared by reacting a compound [Im] or its salt with a azide compound.

Suitable azide compound may be alkali metal azide [e.g. sodium azide, potassium azide, etc.], alkaline earth metal azide [e.g. calcium azide, etc.], hydrogen azide and the like.

The reaction is usually carried out in a conventional solvent such as tetrahydrofuran, dioxane, N,N-dimethylformamide or any other organic solvent which does not adversely influence the reaction.

The reaction temperature is not critical, and the reaction can be carried out warming to heating.

PROCESS 22

The compound [I-12] can be prepared by the following methods.

Namely, (1) the compound [VI] or its salt is firstly reacted with a nitrite compound, and then (2) the resultant product is reacted with cuprous halide.

Suitable salt of the compound [VI] may be the same as those exemplified for the compound [I].

Suitable nitrite compound may be alkali metal nitrite [e.g. sodium nitrite, potassium nitrite, etc.], alkyl nitrite [e.g. tert-butyl nitrite, etc.]and the like.

Suitable cuprous halide may be cuprous chloride, cuprous bromide and the like.

In the first step, the reaction is preferably carried out in the presence of an acid [e.g. sulfuric acid, etc.].

The reaction is usually carried out in a solvent such as water, tetrahydrofuran, dioxane, acetonitrile or any other organic solvent which does not adversely influence the reaction, or a mixture thereof.

The reaction temperature is not critical and the reaction can be carried out under cooling to warming.

In the second step, the reaction is preferably carried out in the presence of alkali metal halide [e.g. sodium bromide, etc.] and an inorganic acid [e.g. hydrobromic acid, etc.].

The reaction is usually carried out in a solvent such as water, tetrahydrofuran, dioxane or any other organic solvent which does not adversely influence the reaction.

The reaction temperature is not critical and the reaction can be carried out warming to heating.

PROCESS 23

The compound [Im] or its salt can be prepared by reacting a compound [1-12] or its salt with cuprous cyanide.

The reaction is usually carried out in a conventional solvent such as pyridine, quinoline, N,N-dimethylformamide, N-methylpyrrolidone or any other organic solvent which does not adversely influence the reaction, or without solvent.

The reaction temperature is not critical, and the reaction can be carried out warming to heating.

PROCESS 24

The compound [I-12] or its salt can be prepared by reacting a compound [I-13] or its salt with halogen.

The reaction is usually carried out in a conventional solvent such as dichloromethane, chloroform, carbon tetrachloride or any other organic solvent which does not adversely influence the reaction.

The reaction temperature is not critical, and the reaction can be carried out cooling to warming.

PROCESS 25

The compound [Ia] or its salt and/or the compound [Ib] or its salt can be prepared by reacting a compound [VII] or its salt with a compound [III] or its salt.

Suitable salts of the compounds [III] or [VII] may be the same as those exemplified for the compound [I].

This reaction can be carried out in substantially the same manner as that of Process 1, and therefore the reaction mode and reaction conditions (e.g. solvent, reaction temperature, etc.) of this reaction are to be referred to those as explained in Process 1.

The compounds obtained by the above processes can be isolated and purified by a conventional method such as pulverization, recrystallization, column chromatography, reprecipitation, or the like.

The object compound [I] and pharmaceutically acceptable salts thereof possess strong antiinflammatory, analgesic and antithrombotic activities, and are useful for the treatment and/or prevention of inflammatory conditions, various pains, collagen diseases, autoimmune diseases, various immunity diseases and thrombosis in human beings or animals, and more particularly to methods for the treatment and/or prevention of inflammation and pain in joint and muscle [e.g. rheumatoid arthritis, rheumatoid spondylitis, osteoarthritis, gouty arthritis, etc.], inflammatory skin condition [e.g. sunburn, eczema, etc.], inflammatory eye condition [e.g. conjunctivitis etc.], lung disorder in which inflammation is involved [e.g. asthma, bronchitis, pigeon fancier's disease, farmer's lung, etc.], condition of the gastrointestinal tract associated with inflammation [e.g. aphthous ulcer, Chrohn's disease, atropic gastritis, gastritis varialoforme, ulcerative colitis, coeliac disease, regional ileitis, irritable bowel syndrome, etc.], gingivitis, inflammation, pain and tumescence after operation or injury, pyresis, pain and other conditions associated with inflammation, particularly those in which lipoxygenase and cyclooxygenase products are a factor, systemic lupus erythematosus, scleroderma, polymyositis, periarteritis nodosa, rheumatic fever, Sjögren's syndrome, Behcet disease, thyroiditis, type I diabetes, nephrotic syndrome, aplastic anemia, myasthenia gravis, uveitis, contact dermatitis, psoriasis, Kawasaki disease, sarcoidosis, Hodgkin's disease and the like. Additionally, the object compound is expected to be useful as therapeutical and/or preventive agents for cardiovascular or cerebrovascular diseases, the diseases caused by hyperglycemia and hyperlipemia.

In order to illustrate the usefulness of the object compound [I], the pharmacological test data of the compound [I] are shown in the following.

[A] ANTIINFLAMMATORY ACTIVITY

Effect on adjuvant arthritis in rats :

(i) Test Method :

Ten female Sprague-Dawley rats were used per group. A dose of 0.5 mg of Mycobacterium tuberculosis (strain Aoyama B) suspended in 0.05 ml of liquid paraffin was injected subcutaneously in the right hand paw. The injection of mycobacterial adjuvant produced local inflammatory lesions (primary lesion) and then about 10 days later, secondary lesions in both the injected and uninjected paws. The difference in volumes of both paws before and after adjuvant injection was the measure of arthritis. The drug was given orally once a day for 23 consecutive days from day 1.

(ii) Test Results:

| Test compound (Example No.) | Dose (mg/kg) | Inhibition of secondary lesion (uninjected paw) % |
| --- | --- | --- |
| 6 | 10 | 95.6 |
| 11-3) | 10 | 100 |
| 15-6) | 3.2 | 94.3 |
| 17-1) | 3.2 | 80.6 |
| 24 | 3.2 | 80.6 |
| 24 | 3.2 | 87.4 |
| 33-2) | 3.2 | 87.1 |
| 36 | 3.2 | 84.2 |
| 37-2) | 3.2 | 81.7 |
| 45-8) | 3.2 | 80.8 |
| Ibuprofen | 10 | 24.7 |

[B] ANALGESIC ACTIVITY

Inflammatory hyperalgesia induced by brewer's yeast in rats :

(i) Test Method :

Ten male Sprague Dawley rats were used per group. 0.1 ml of 5% brewer's yeast suspended in 0.5% methylcellulose was injected into the right hind paw. The pain threshold was determined 3 hours after yeast injection, by applying pressure to the foot and reading the pressure at which the rat withdrew the foot.

The drugs were given orally 2 hours after yeast injection. The pain threshold in the treated animals was compared with that in the control animals.

(ii) Test Results :

| Test compound (Example No.) | Dose (mg/kg) | Relative potency (Control = 1.0) |
| --- | --- | --- |
| 6 | 32 | 1.34 |
| 11-3) | 32 | 1.35 |
| 24 | 10 | 1.44 |

[C] ANTI-RHEUMATIC ACTIVITY

Effect on collagen induced arthritis in mice :

(i) Test Method :

Eight male DBA/1 mice were used per group. Type II bovine collagen was solublized in 0.1M acetic acid and emulsified in complete Freund's adjuvant (CFA . Mice were primed with 0.2 mg of Type II collagen in CFA intradermally at the base of the tail. Mice were challenged after 21 day with the same procedure. From 10 day after challenge, drug was administered orally once a day for 3 weeks and mice were inspected weekly for visual signs of arthritis. An arthritis index was used to grade limb 0-3, representing joint swelling and erythema (Grade 1), visible joint disorder (Grade 2 and detectable joint ankylosis (Grade 3).

(ii) Test Results :

| Test compound (Example No.) | Dose (mg/kg) | Inhibition of arthritis index (%) |
| --- | --- | --- |
| 6 | 10 | 78.6 |
| 11-3) | 10 | 91.7 |
| 15-6) | 10 | 98.9 |
| 24 | 10 | 90.5 |
| 33-2) | 10 | 92.4 |
| 45-8) | 10 | 83.5 |

[D] ANTITHROMBOTIC ACTIVITY

Effect on platelet aggregation induced by collagen :

(i) Test Method :

Platelet rich plasma (PRP) which contains $3 \times 10^8$ platelets/ml was prepared from human blood. To the 245 $\mu$l of PRP, 5 $\mu$l of drug solution* was added, and then stirred for 2 min at 37° C. To the solution 5 $\mu$l of collagen (0.5 $\mu$g/ml) was added as an aggregation inducer. Aggregation was measured by using an aggregometer (NKK HEMA-TRACER 1). Activities of inhibitors (test compounds) were expressed as $IC_{50}$ values i.e. doses required to inhibit the platelet aggregation responses by 50%.

Drug solution* - - - Test compounds were dissolved in dimethylsulfoxide.

(ii) Test Result :

| Test compound (Example No.) | $IC_{50}$ (M) |
| --- | --- |
| 6 | $5.3 \times 10^{-6}$ |

[E] Effect on Delayed Type Hypersensitivity (DTH) Response to bovine type II collagen (i) Test Method :

Seven male DBA/1 mice were used for this test. The mice were sensitized at tail base with 125 $\mu$g type II collagen emulsified in complete Freund's adjuvant containing Mycobacterium tuberculosis strain H37Rv (Wako Pure Chemical Industries Ltd., Osaka, Japan). Two weeks' later, a 0.04 ml challenge dose of 2.5 mg/ml type II collagen in phosphate buffered saline (PBS) was injected into the plantar region of the right hind foot and 0.04 ml PBS into the left hind foot to act as a control. Twenty four hours after challenge, the volume of both hind feet were measured with a volume meter (Muromachi MK-550).

The drug was administered orally on consecutive days except holidays, starting from the sensitization.

Data was expressed by per cent inhibition compared with vehicle control for each study.

(ii) Test Results :

| Test compound (Example No.) | Dose (mg/kg) | | |
| --- | --- | --- | --- |
| | 0.32 | 1.0 | 3.2 |
| 6 | 53.4 | 61.5 | 74.3 |
| 15-2) | 55.4 | 70.9 | 69.6 |
| 24 | 45.9 | 66.9 | 75.7 |

For therapeutic purpose, the compound [I] and a pharmaceutically acceptable salt thereof of the present invention can be used in a form of pharmaceutical preparation containing one of said compounds as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, inhalant, suppositories, solution, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average singele dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

The following Preparations and Examples are given for the purpose of illustrating this invention.

PREPARATION 1

A mixture of 4-(methylthio)acetophenone 1 g) and sodium hydride (60%; 288 mg) in N,N-dimethylformamide (7 ml) was stirred at ambient temperature for 30 minutes. The mixture was cooled to 0° C., and diethyl oxalate (0.98 ml) was added dropwise to the mixture. The resulting mixture was stirred at ambient temperature for 3 hours, poured into ice-water and acidified with dilute hydrochloric acid. The precipitates were filtered, washed with water, and dried under reduced pressure to give a pale brown powder of ethyl 4-[4-(methylthio)phenyl]-2,4-dioxobutanoate (1.6 g).

mp: 91°-97° C.
IR (Nujol 3420, 1735, 1620, 1595, 1515 cm$^{-1}$
NMR (DMSO-d$_6$, δ): 1.29 (3H, t, J=7Hz) , 2.54 (3H, s), 4.25 (2H, q, J=7Hz), 6.78 (1H, s), 7.35 (2H, d, J=8.5Hz), 7.91 (2H, d, J=8.5Hz)
Mass (m/z) : 266 (M+), 193

The following compounds (Preparations 2-1 to 2-7)) were obtained according to a similar manner to that of Preparation 1.

PREPARATION 2

(1) 1-[4-(Methylthio)phenyl]-4,4,4-trifluorobutane-1,3-dione.
mp : 79°-83° C.
IR (Nujol 1590 (broad), 1490 cm$^{-1}$
NMR (DMSO-d$_6$, δ) 2.57 3H, s , 7.0 (1H, s), 7.42 (2H, d, J=8.6Hz), 8.06 2H, d, J=8.6Hz)
Mass (m/z) : 262 (M+)

(2) Ethyl 4-[5-(methylthio)-2-thienyl]-2,4-dioxobutanoate.
mp : 33°-45° C.
IR (Nujol) : 1730, 1620, 1560, 1510 cm$^{-1}$
NMR (CDCl$_3$, δ) : 1.42 (3H, t, J=7Hz), 2.64 (3H, s), 4.38 (2H, q, J=7Hz), 6.84 (1H, s), 6.95 (1H, d, J=4Hz), 7.27 (1H, s), 7.63 (1H, d, J=4Hz)
Mass (m/z) : 272 (M+)

(3) Ethyl 4-[4-(formylamino)phenyl]-2,4-dioxobutanoate.
mp : 171°-174° C. (dec.)
IR (Nujol) : 3300, 1730, 1700, 1600, 1525 cm$^{-1}$
Mass (m/z) : 263 (M+)

(4) Ethyl 4-(4-acetylphenyl)-2,4-dioxobutanoate.
mp 81°-82° C.
IR (Nujol) : 1725, 1690, 1600 cm$^{-1}$
NMR (CDCl$_3$, δ) 1.43 (3H, t, J=7Hz), 2.67 (3H, s), 4.42 (2H, q, J=7Hz), 7.11 (1H, s), 8.0-8.2 4H, m), 15.13 (1H, s)
Mass (m/z) : 262 (M+)

(5) Ethyl 4-[3,5-di(t-butyl)-4-hydroxyphenyl]-2,4-dioxobutanoate.
mp : 128-°131° C.
IR (Nujol 3600, 1730, 1630, 1595 cm$^{-1}$
NMR (DMSO-d$_6$, δ) : 1.35 (3H, t, J=7Hz), 1.43 (18H, s), 4.32 (2H, q, J=7Hz), 6.99 (1H, s), 7.74 (2H, s)

(6) 4-Fluoro-1-[4-(methylthio)phenyl]butan-1,3-dione.
mp : 64-°68° C.
IR (Nujol) : 1675, 1595, 1550 cm$^{-1}$
NMR (CDCl$_3$, δ): 2.49 (3H, s), 4.33 (1H, s), 5.11 (1H, s), 6.38 (1H, d, J=3Hz),̇7.17 (2H, d, J=9Hz), 7.74 (2H, d, J=9Hz)

(7) 4,4-Difluoro-1-[4-(methylthio)phenyl]butan-1,3-dione.
IR (Nujol) : 1640, 1595 cm$^{-1}$
Mass (m/z) : 244 (M+)

PREPARATION 3

A solution of diethyl cyanomethylphosphonate (5.3 ml) in tetrahydrofuran (10 ml) was added dropwise to an ice-cooled mixture of sodium hydride (60%, 1.3 g) in tetrahydrofuran (40 ml). The mixture was stirred at 5° C. for 15 minutes. To the resulting mixture was added a solution of 4-(methylthio)benzaldehyde (5 g) in tetrahydrofuran (10 ml) at 5 to 10° C. The mixture was stirred at ambient temperature for 5 hours, diluted with ethyl acetate, and washed with water. The organic layer was dried and concentrated under reduced pressure. The residue was washed with a small amount of ether and dried to give pale brown crystals of 3-[4-(methylthio)phenyl]acrylonitrile (4.7 g).

IR (Nujol) : 2220, 1615, 1590, 1490 cm$^{-1}$
NMR (DMSO-d$_6$, δ) : 2.51 (3H, s), 6.40 (1H, d, J=16.7Hz , 7.2-7.7 (5H, m)
Mass [m/z) : 175 (M+)

PREPARATION 4

4-Fluorophenylhydrazine hydrochloride 4 g) was added to a solution of sodium (1.13 g) in ethanol (50 ml), and the mixture was refluxed for 1 hour. To the cooled mixture was added 3-[4-(methylthio)phenyl]acrylonitrile (4.3 g), and the resulting mixture was refluxed overnight. Ethyl acetate and water were added, and the organic layer was separated, dried and concentrated. The oily residue (7.6 g) was purified by column chromatography on silica gel (76 g) eluting with a mixture of toluene and ethyl acetate (2:1) to give brown crystals of 4,5-dihydro-1-(4-fluorophenyl)-5-[4-(methylthio)phenyl]pyrazol-3-amine (5 g).

mp : 100°-110° C. Mass (m/z) : 301 (M+)

PREPARATION 5

A mixture of 4,5-dihydro-1-(4-fluorophenyl)-5-[4-(methylthio)phenyl]pyrazol-3-amine (1 g) and manganese (IV) oxide (1.16 g) in dichloromethane (100 ml) was stirred at ambient temperature for 2 hours. The insoluble was filtered and the filtrate was concentrated to dryness. The residue (1 g) was purified by column chromatography on silica gel (16 g) eluting with a mixture of chloroform and ethyl acetate (5:1 to give a pale brown powder of 1-(4-fluorophenyl)-5-[4-(methylthio)phenyl]pyrazol-3-amine (0.64 g).

IR (Nujol 3400, 1600, 1565, 1515 cm$^{-1}$
NMR (DMSO-d$_6$δ) : 2.46 (3H, s), 4.97 (2H, s), 5.82 (1H, s), 7.0-7.3 (8H, m)
Mass (m/z) : 299 (M+)

PREPARATION 6

A solution of sodium nitrite (3.6 g) in water (18 ml) was added dropwise to an ice-salt cooled solution of 4-fluoro-2-nitroaniline 7 g) in conc. hydrochloric acid (45 ml) over a 30 minutes interval. The mixture was stirred at 0° C. for 30 minutes. Then to the mixture was added dropwise a solution of stannous chloride dihydrate (28.6 g) in conc. hydrochloric acid (24 ml) below 5° C. over an hour interval. The precipitates were collected by filtration and washed with ether to give crystals of 4-fluoro-2-nitrophenylhydrazine hydrochloride 4.4 g).

mp : >260° C.

Mass (m/z) : 171 (M+)

PREPARATION 7

A solution of carbon disulfide 4.6 g) in tetrahydrofuran (60 ml was added dropwise to a mixture of 4-(methylthio)acetophenone (10 g) and 60% sodium hydride (4.8 g) in tetrahydrofuran (100 ml) at ambient temperature over an hour interval. The mixture was stirred at 40° C. for 2 hours, and a solution of iodomethane (17.1 g) in tetrahydrofuran (60 ml) was added to the mixture. The resulting mixture was stirred at 40° C. for 1 hour and under reflux for 1 hour. Water and chloroform were added to the mixture. The organic layer was washed with water, dried, and evaporated in vacuo. The residue was washed with methanol to give crystals of 1-[4-(methylthio)phenyl]-3,3-bis(methylthio)-2-propen-1-one (10.5 g).

mp : 119°-122° C.

IR (Nujol) : 1620, 1590, 1550, 1495 cm$^{-1}$

NMR (CDCl$_3$, δ) 2.52 3H, s , 2.53 (3H, s), 2.56 (3H, s), 6.74 (1H, s), 7.26 (2H, d, J=7Hz), 7.83 (2H, d, J=7Hz)

Mass (m/z) : 270 (M+)

PREPARATION 8

A mixture of ethyl 4-(4-tolyl)-2,4-dioxobutanoate (4.7 g) and 4-fluorophenylhydrazine hydrochloride (3.6 g) in dioxane (35 ml) and ethanol (35 ml) was refluxed for 5 hours. The mixture was filtered and the filtrate was concentrated in vacuo. The oily residue (8 g) was purified.by column chromatography on silica gel (130 g) eluting with chloroform to give an oil of ethyl 1-(4-fluorophenyl)-5-(4-tolyl)pyrazole-3-carboxylate (2.7 g).

IR (Film) : 1720, 1610, 1510 cm$^{-1}$

NMR (CDCl$_3$, δ) 1.42 (3H, t, J=7Hz), 2.31 (3H, s), 4.40 (2H, q, J=7Hz), 6.8-7.4 (9H, m)

The following compounds (Preparations 9-1) to 9-3)) were obtained according to a similar manner to that of Preparation 8.

PREPARATION 9

(1) Ethyl 1-(4-fluorophenyl)-5-(4-methoxyphenyl)-pyrazole-3-carboxylate.

mp : 91°-93° C.

IR (Nujol)) : 1715, 1610, 1510 cm$^{-1}$

NMR (CDCl$_3$, δ) 1.38 (3H, t, J=7Hz), 3.81 3H, s), 4.45 (2H, q, J=7Hz), 6.8-7.4 (9H, m)

Mass (m/z) : 340 (M+)

(2) Ethyl 1,5-bis(4-methoxyphenyl)pyrazole-3-carboxylate.

IR (Film) : 1730, 1610, 1510 cm$^{-1}$ (3) Ethyl 5-(4-cyanophenyl)-1-(4-fluorophenyl)-pyrazole-3-carboxylate.

mp 147°-148° C.

IR (Nujol) : 2230, 1735, 1610, 1510 cm$^{-1}$

NMR (CDCl$_3$, δ) 1.43 (3H, t, J=7Hz), 4.46 (2H, q, J=7Hz), 7.0-7.8 (9H, m)

Mass (m/z) : 335 (M+)

PREPARATION 10

A mixture of ethyl 1-(4-fluorophenyl)-5-(4-tolyl)-pyrazole-3-carboxylate (2.7 g) and potassium hydroxide (1.1 g) in methanol (40 ml) was refluxed for 30 minutes. The solvent was evaporated, and the residue was dissolved in water and washed with ethyl acetate. The aqueous layer was acidified with dilute hydrochloric acid and extracted with ethyl acetate. The extract was washed with water, dried, and concentrated, giving crystals of 1-(4-fluorophenyl)-5-(4-tolyl)pyrazole-3-carboxylic acid (2.1 g).

mp : 170°-173° C.

IR (Nujol) : 2750, 2600, 1690, 1600, 1510 cm$^{-1}$

Mass (m/z) : 296 (M+)

EXAMPLE 1

A mixture of ethyl 4-[4-(methylthio)phenyl]-2,4-dioxobutanoate (1 g) and 4-fluorophenylhydrazine hydrochloride (0.67 g) in ethanol (10 ml) and dioxane (10 ml) was refluxed for 5 hours. The solvent was evaporated, and the residue was dissolved in chloroform and washed with water. The organic layer was dried over magnesium sulfate and concentrated. The residue (1.6 g) was purified by column chromatography on silica gel (30 g) eluting with a mixture of toluene and ethyl acetate (20:1) to give ethyl 1-(4-fluorophenyl)-3-[4-(methylthio)phenyl]pyrazole-5-carboxylate (0.11 g).

mp : 100°-104° C.

IR (Nujol) : 1730, 1600, 1515 cm$^{-1}$

NMR (CDCl$_3$, δ) : 1.29 (3H, t, J=7Hz), 2.51 (3H, s), 4.27 (2H, q, J=7Hz , 7.1-7.9 (9H, m) Mass (m/z) : 356 (M+)

Furthermore, the second fraction which eluted with the same solvent, was concentrated in vacuo to give pale brown crystals of ethyl 1-(4-fluorophenyl)-5-[4-(methylthio)phenyl]pyrazole-3-carboxylate (1.1 g).

mp : 100°-102° C.

IR (Nujol 1710, 1600, 1510 cm$^{-1}$

NMR (CDCl$_3$, δ) : 1.42 (3H, t, J=7Hz), 2.48 (3H, s), 4.45 (2H, q, J=7Hz), 7.0-7.4 (9H, m)

Mass (m/z) : 356 (M+)

EXAMPLE 2

A solution of ethyl 1-(4-fluorophenyl)-5-[4-methylthio)phenyl]pyrazole-3-carboxylate (0.95 g) and 30% hydrogen peroxide solution (0.79 ml) in acetic acid (9.5 ml) was stirred at 70° C. for 3 hours. The mixture was cooled in an ice-water bath, and the precipitates were filtered and washed with ethanol to give colorless crystals of ethyl 1-(4-fluorophenyl)-5-[4-methylsulfonyl)-phenyl]pyrazole-3-carboxylate (0.94 g).

mp : 210°-212° C.

IR (Nujol) : 1715, 1600, 1515 cm$^{-1}$

NMR (DMSO-d$_6$, δ) 1.32 (3H, t, J=7Hz), 3.25 (3H, s), 4.35 (2H, q, J=7Hz), 7.3-7.6 7H, m), 7.92 (2H, d, J=8 5Hz)

Mass (m/z) : 338 (M+)

EXAMPLE 3

A mixture of ethyl 1-(4-fluorophenyl)-5-[4-(methylsulfonyl)phenyl]pyrazole-3-carboxylate (4.4 g) and 4N sodium hydroxide (5.7 ml) in tetrahydrofuran (20 ml), ethanol (10 ml and dioxane 20 ml) was stirred at ambient temperature overnight. Water (50 ml) was added, and the mixture was acidified with hydrochloric acid. The precipitates were filtered and washed with water to give colorless crystals of 1-(4-fluorophenyl)-5-[4-(methylsulfonyl)phenyl]pyrazole-3-carboxylic acid (4.1 g).

mp : 232°-234° C.

IR (Nujol) : 1695, 1600, 1510 cm$^{-1}$

NMR (DMSO-d$_6$, δ) : 3.25 (3H, s), 7.2-7.6 (7H, m), 7.92 (2H, d, J=8.3Hz), 13.1 (1H, s)

Mass (m/z) : 360 (M+)

EXAMPLE 4

A mixture of 1-(4-fluorophenyl)-5-[4-(methylsulfonyl)phenyl]pyrazole-3-carboxylic acid (1.1 g) and phosphorus pentachloride (0.67 g) in toluene (16 ml) and tetrahydrofuran 9 ml) was stirred at ambient temperature for 2 hours. The insoluble material was filtered and the filtrate was concentrated to give an oil of 1-(4-fluorophenyl)-5-[4-(methylsulfonyl)phenyl]pyrazole-3-carbonyl chloride (1.37 g).

IR (Film) : 1760, 1605, 1510 cm$^{-1}$

A mixture of 25% methylamine aqueous solution (2 ml), ice-water (5 ml and tetrahydrofuran (10 ml was added to the above acid chloride. The mixture was stirred overnight. The precipitates were filtered, and the filtrate was extracted with ethyl acetate. The extract was washed with water, dried and concentrated. The residue (0.21 g) and the precipitates (0.83 g) were combined, and recrystallized from a mixture of ethyl acetate and ethanol to give colorless crystals of 1-(4-fluorophenyl)-N-methyl-5-[4-(methylsulfonyl)phenyl]-pyrazole-3-carboxamide (1.0 g).

mp : 271°-273° C.

IR (Nujol 3400, 1660, 1605, 1550, 1535, 1510 cm$^{-1}$

NMR (DMSO-d$_6$, δ) : 2.78 (3H, d, J=4.6Hz), 3.25 (3H, s), 7.16 (1H, s), 7.3-7.6 (6H, m), 7.91 (2H, d, J=8.3Hz), 8.35 (1H, q, J=4.6Hz)

Mass (m/z) : 373 (M$^+$)

The following compounds (Examples 5-1 to 5-12)) were obtained according to a similar manner to that of Example 4.

EXAMPLE 5

(1) 1-(4-Fluorophenyl)-5-[4-(methylsulfonyl)phenyl]-pyrazole 3-carboxamide.

mp : 215°-217° C.

IR (Nujol) : 3470, 3200, 1680, 1600, 1515 cm$^{-1}$

NMR (DMSO-d$_6$, δ) : 3.25 (3H, s), 7 16 (1H, s), 7.2-7.6 (7H, m), 7.77 (1H, s), 7.91 (2H, d, J=8.5Hz)

Mass (m/z) : 359 (M$^+$), 341

(2) 1-(4-Fluorophenyl)-N,N-dimethyl-3-[4-(methylsulfonyl)phenyl]pyrazole-5-carboxamide.

mp : 192°-193° C.

IR( Nujol 1640, 1605, 1510 cm$^{-1}$

NMR (DMSO-d$_6$, δ) : 2.95 (3H, s), 2.96 (3H, s), 3.27 (3H, s), 7.3-8.3 (9H, m)

Mass (m/z) : 387 (M$^+$)

(3) 1-(4-Fluorophenyl)-3-[4-(methylsulfonyl)phenyl]-pyrazole-5-carboxamide.

mp : 270°-271° C.

IR (Nujol) : 3380, 3200, 1670, 1625, 1605, 1510 cm$^{-1}$

NMR (DMSO-d$_6$, δ) : 3.26 (3H, s), 7.2-8.2 (11H, m)

Mass (m/z) : 359 (M$^+$)

(4) 5-[3,5-Di(t-butyl)-4-hydroxyphenyl]-1-(4-fluorophenyl)pyrazole-3-carboxamide.

mp : 247°-249° C.

IR (Nujol 3650, 3500, 3350, 1660, 1510 cm$^{-1}$

NMR (DMSO-d$_6$, δ) : 1.26 18H, s), 6.96 (3H, s), 7.2-7.7 (6H, m)

Mass (m/z) : 409 (M$^+$)

(5) N-Phenyl-1-(4-fluorophenyl)-5-[4-(methylthio)-phenyl]pyrazole-3-carboxamide.

mp : 200°-205° C. (dec.)

IR (Nujol) : 3400, 1680, 1595, 1530, 1510 cm$^{-1}$

NMR DMSO-d$_6$, δ) 2.46 (3H, s), 7.0-7.6 (12H, m), 7.83 (2H, d, J=8Hz), 10.19 (1H, s)

Mass (m/z) : 409 (M$^+$)

(6) 1-(4-Fluorophenyl)-5-[4-(methylthio)phenyl]-3-(1-pyrrolidinylcarbonyl)pyrazole.

mp : 139°-140° C.

IR (Nujol 1615, 1515 cm$^{-1}$

NMR (CDCl$_3$, δ) : 1.8-2.1 (4H, m), 2.48 (3H, s), 3.70 (2H, t, J=6Hz), 3.98 (2H, t, J=6Hz), 6.9-7.4 (9H, m)

Mass (m/z) : 381 (M$^+$)

(7) N-Cyclopropyl-1-(4-fluorophenyl)-5-[4-(methylthio)phenyl]pyrazole-3-carboxamide.

mp 147°-148° C.

IR (Nujol) : 3360, 1675, 1600, 1510 cm$^{-1}$

NMR (CDCl$_3$, δ) : 0.6-0.9 (4H, m), 2.48 (3H, s), 2.8-3.0 (1H, m), 7.0-7.4 (9H, m)

Mass (m/z) : 367 (M$^+$)

(8) 1-(4-Fluorophenyl)-3-(4-methyl-1-piperazinylcarbonyl)-5-[4-(methylsulfonyl) phenyl]pyrazole.

mp : 170°-173° C.

IR (Nujol) : 1620, 1520, 1500 cm$^{-1}$

NMR (CDCl$_3$, δ) : 2.34 (3H, s), 2.4-2.6 (4H, m), 3.08 (3H, s), 3.8-4.2 (4H, m), 6.9-7.5 (7H, m), 7.91 (2H, d, J=8Hz)

Mass (m/z) : 442 (M$^+$)

(9) N-Hydroxy-N-methyl-1-(4-fluorophenyl)-5-[4-(methylsulfonyl)phenyl]pyrazole-3-carboxamide.

mp 185°-188° C. (dec.)

IR (Nujol) : 1630, 1605, 1510 cm$^{-1}$

NMR (CDCl$_3$, δ) : 3.09 (3H, s), 3.86 (3H, s), 7.0-7.5 (7H, m), 7.91 (2H, d, J=8Hz)

Mass (m/z) : 389 (M$^+$)

(10) N-{1-(4-Fluorophenyl)-5-[4-(methylsulfonyl)-phenyl]-3-pyrazolylcarbonyl}glycin.

mp : 258°-260° C. (dec.)

IR (Nujol) : 3420, 1720, 1645, 1560, 1510 cm$^{-1}$

NMR (DMSO-d$_6$, δ) : 3.25 (3H, s), 3.89 (2H, d, J=6Hz), 7.20 (1H, s), 7.3-7.6 (6H, m), 7.92 (2H, d, J=8Hz), 8.50 (1H, t, J=6Hz)

Mass (m/z) : 417 (M$^+$)

(11) N-Methyl-1-[4-(N-formylmethylamino)phenyl]-5-[4-(methylsulfonyl)phenyl]pyrazole-3-carboxamide.

IR (Nujol) : 3350, 1660, 1605, 1550, 1515 cm$^{-1}$

Mass (m/z) : 412 (M$^+$)

(12) N,N-Dimethyl-1-[4-(N-formylmethylamino)-phenyl]-5-[4-(methylsulfonyl)phenyl]pyrazole-3-carboxamide.

Mass (m/z) 426 (M$^+$)

EXAMPLE 6

A mixture of 1-(4-fluorophenyl)-5-[4-(methylsulfonyl)phenyl]pyrazole-3-carboxamide (2.7 g) and methanesulfonyl chloride (3.4 ml) in pyridine (25 ml) was stirred at 50° C. for 6 hours. The solvent was evaporated, and ethyl acetate and water were added to the residue. The precipitates were filtered and washed with water and ethyl acetate. The filtrate was separated, and the organic layer was washed with dilute hydrochloric acid, dried and concentrated to dryness. The residue and the former precipitates were combined and recrystallized from a mixture of ethanol and ethyl acetate to give colorless crystals of 1-(4-fluorophenyl)-5-[4-(methylsulfonyl)phenyl]pyrazole-3-carbonitrile (2.4 g).

mp : 194°-196° C.

IR (Nujol) : 2240, 1600, 1515 cm$^{-1}$

NMR (DMSO-d$_6$, δ) : 3.25 (3H, s), 7.3-7.6 (7H, m), 7.95 (2H, d, J=6.7Hz)

Mass (m/z) : 341 (M$^+$)

The following compounds (Examples 7-1) to 7-4)) were obtained according to a similar manner to that of Example 3.

EXAMPLE 7

(1) 1) 1-(4-Fluorophenyl)-5-[4-(methylthio)phenyl]-pyrazole-3-carboxylic acid.

IR (Nujol) : 3500, 1695, 1600, 1515 cm$^{-1}$ (2) 1-(4-Fluorophenyl)-3-[4-(methylsulfonyl)phenyl]-pyrazole-5-carboxylic acid.

mp : 259°-260° C. (dec.)

IR (Nujol) : 1705, 1605, 1515 cm$^{-1}$

NMR (DMSO-d$_6$, δ) : 3.26 (3H, s), 7.3-8.3 (9H, m)

Mass (m/z) : 360 (M+)

(3) 5-[3,5-Di(t-butyl)-4-hydroxyphenyl]-1-(4-fluorophenyl)pyrazole-3-carboxylic acid.
mp : 239°-242° C.
IR (Nujol) : 3550, 1690, 1510 cm$^{-1}$
NMR (DMSO-d$_6$, δ) : 1.25 (18H, s), 6.96 (2H, s), 7.03 (1H, s), 7.25-7.45 (4H, m)
Mass (m/z) : 410 (M+), 395

(4) 1-[4-(N-Formylmethylamino)phenyl]-5-[4-(methylsulfonyl)phenyl]pyrazole-3-carboxylic acid.
IR (Nujol) : 1720, 1665, 1605, 1520 cm$^{-1}$
Mass (m/z) : 399 (M+)

EXAMPLE b 8

A mixture of 1-(4-fluorophenyl)-5-[4-(methylthio)phenyl]pyrazole-3-carboxylic acid (3 g) and 1,1'-carbonyldiimidazole (1.6 g) in tetrahydrofuran (39 ml) was refluxed for 1 hour. Dimethylamine hydrochloride (1.04 g) and potassium carbonate (1.33 g) were added, and the resulting mixture was stirred and refluxed for 3 hours. The mixture was diluted with ethyl acetate, washed with water, an aqueous solution of sodium bicarbonate, dilute hydrochloric acid and water, successively, dried and concentrated to give a pale brown oil of 1-(4-fluorophenyl)-N,N-dimethyl-5-[4-(methylthio)phenyl]pyrazole-3-carboxamide (2.6 g).
IR (Film) : 1620, 1510 cm$^{-1}$

EXAMPLE b 9

A mixture of 1-{4-fluorophenyl)-N,N-dimethyl-5-[4-methylthio)phenyl]pyrazole-3-carboxamide (1 g) and m-chloroperbenzoic acid (1.8 g) in dichloromethane (17 ml) was stirred at ambient temperature overnight. The insoluble was filtered, and the filtrate was washed with an aqueous solution of sodium bicarbonate, dried and concentrated to dryness. The residual oil (1.4 g) was purified by column chromatography on silica gel (30 g) eluting with a mixture of chloroform and methanol 20:1). The oil obtained (1.0 g) was crystallized from ether to give colorless crystals of N,N-dimethyl-1-(4-fluorophenyl)-5-[4-(methylsulfonyl)phenyl]pyrazole-3carboxamide (0.69 g).
mp . 171°-173° C.
IR (Nujol) : 1620, 1510 cm$^{-1}$
NMR (DMSO-d$_6$, δ) : 3.02 (3H, s), 3.25 (3H, s), 3.32 (3H, s), 7.08 (1H, s), 7.2-8.0 (8H, m)
Mass (m/z) : 387 (M+)

EXAMPLE 10

A mixture of 1-(4-fluorophenyl)-N,N-dimethyl-5-[4-(methylthio)phenyl]pyrazole-3-carboxamide (1.6 g) and lithium aluminum hydride (0.34 g) in ether (8.5 ml) and benzene (13 ml) was stirred and refluxed for 2 hours. 4N Sodium hydroxide (10 ml) was added dropwise and ethyl acetate (20 ml) was added to the mixture. The insoluble was filtered and the filtrate was separated. The organic layer was washed with water, dried and concentrated. The residue (1.2 g) was purified by column chromatography on silica gel (30 g) eluting with a mixture of ethyl acetate and methanol (5:1) to give a pale brown oil of 3-(N,N-dimethylaminomethyl)-1-(4-fluorophenyl)-5-[4-(methylthio)phenyl]pyrazole (0.69 g).
IR (Film) : 2820, 2770, 1600, 1560, 1510 cm$^{-1}$
Mass (m/z) : 341 (M+), 298

The following compounds (Examples 11-1) to 11-3)) were obtained according to a similar manner to that of Example 9.

EXAMPLE 11

(1) 3-(N,N-Dimethylaminomethyl)-1-(4-fluorophenyl)-5-[4-(methylsulfonyl)phenyl]pyrazole hydrochloride.
mp : 157°-160° C. (dec.)
IR (Nujol) : 3350, 2580, 1600, 1510 cm$^{-1}$
NMR (DMSO-d$_6$, δ) : 3.25 (3H, s), 3.54 (6H, s), 4.99 (2H, s), 7.07 (1H, s), 7.2-8.0 (8H, m), 12.9 (1H, s)
Mass (m/z) : 373 (M+), 330

(2) Ethyl 1-(4-fluorophenyl)-3-[4-(methylsulfonyl)phenyl]pyrazole-5-carboxylate.
mp : 203°-205° C.
IR (Nujol) : 1725, 1605, 1515 cm$^{-1}$
NMR (DMSO-d$_6$, δ) : 1.21 (3H, t, J=7Hz), 3.27 (3H, s), 4.23 (2H, q, J=7Hz), 7.3-8.3 (9H, m)
Mass (m/z) : 388 (M+)

(3) 1-(4-Fluorophenyl)-5-[4-(methylsulfonyl)phenyl]-3-(trifluoromethyl)pyrazole.
mp : 210°-212° C.
IR (Nujol) : 3150, 1605, 1520, 1505 cm$^{-1}$
NMR (DMSO-d$_6$, δ) : 3.26 (3H, s), 7.3-7.6 (7H, m), 7.96 (2H, d, J=8.3Hz)
Mass (m/z) : 384 (M+)

EXAMPLE 22

A mixture of 1-(4-fluorophenyl)-5-[4-(methylsulfonyl)phenyl]pyrazole-3-carboxylic acid (6.4 g) and thionyl chloride (30 ml) in tetrahydrofuran (60 ml) was refluxed for 1 hour and concentrated under reduced pressure, giving 1-(4-fluorophenyl)-5-[4-(methylsulfonyl)phenyl]pyrazole-3-carbonyl chloride.

A solution of diethyl malonate (3.46 g) and ethanol (1.96 ml) in ether (19.6 ml) was added dropwise to a stirred mixture of magnesium 518 mg), ethanol (0.785 ml) and carbon tetrachloride (1.18 ml) in ether (19.6 ml) under nitrogen atmosphere. The resulting mixture was stirred at ambient temperature for 100 minutes and refluxed for 25 minutes. A solution of the above acid chloride in tetrahydrofuran (24 ml) was added portionwise to the mixture. The mixture was stirred at room temperature for 85 minutes and refluxed for 70 minutes. The reaction mixture was poured into 10% sulfuric acid (160 ml) and extracted with ethyl acetate. The extract was washed with water, dried over magnesium sulfate. The solvent was evaporated under reduced pressure to give 3-bis(ethoxycarbonyl)acetyl-1-(4-fluorophenyl)-5-[4(methylsulfonyl)phenyl]pyrazole.

A mixture of sulfuric acid (3.9 ml), acetic acid (23.6 ml) and water (19.6 ml) was added to 3-bis(ethoxycarbonyl)acetyl-1-(4-fluorophenyl)-5-[4-(methylsulfonyl)phenyl]pyrazole. The mixture was refluxed for 5 hours and concentrated. The residue was dissolved in ethyl acetate, and the solution was washed with water, dried and concentrated. The residue was purified by column chromatography on silica gel (150 g) eluting with a mixture of chloroform and ethyl acetate (3:1) to give pale brown crystals of 3-acetyl-1-(4-fluorophenyl)-5-[4-(methylsulfonyl)phenyl]pyrazole (4.2 g).
mp 207°-209° C.
IR (Nujol) : 1690, 1600, 1515 cm$^{-1}$
NMR (DMSO-d$_6$, δ) : 2.57 (3H, s), 3.25 (3H, s), 7.2-8.0 (9H m)
Mass (m/z) : 358 (M+)

EXAMPLE 13

A mixture of 3-acetyl-1-(4-fluorophenyl)-5-[4-(methylsulfonyl)phenyl]pyrazole (1.1 g), thallium (III) nitrate trihydrate (1.6 g) and perchloric acid (70%; 3.3 ml)

in methanol (16 ml) and dioxane (8 ml) was stirred at ambient temperature overnight. The insoluble was filtered, and the filtrate was diluted with chloroform, washed with water, dried and concentrated. The residue (1.6 g) was purified by column chromatography on silica gel (100 g) eluting with a mixture of toluene and ethyl acetate (2:1) to give pale brown crystals of 1-(4-fluorophenyl)-3-(methoxyacetyl)-5-[4-(methylsulfonyl)-phenyl]pyrazole (0.13 g).
mp 151°-154° C.
IR (Nujol) : 1705, 1600, 1510 cm$^{-1}$
NMR (DMSO-$d_6$, δ) : 3.25 (3H, s), 3.39 (3H, s), 4.81 (2H, s), 7.2-8.0 (9H, m)

The following compounds (Examples 14-1) to 14-26)) were obtained according to a similar manner to that of Example 1.

EXAMPLE 14

(1) 1-(4-Fluorophenyl)-5-[4-(methylthio)phenyl]-3-trifluoromethy)pyrazole.
IR (Film) : 1605, 1515, 1500 cm$^{-1}$
NMR (CDCl$_3$, δ) : 2.48 (3H, s), 6.72 (1H, s), 7.0-7.4 (8H, m)
Mass (m/z) : 352 (M$^+$)

(2) Ethyl 5-[4-(methylthio)phenyl]-1-(4-pyridyl)-pyrazole-3-carboxylate hydrochloride.
mp : 181°-186° C.
IR (Nujol) : 1720, 1630, 1600, 1510 cm$^{-1}$
NMR (DMSO-$d_6$, δ) : 1.34 (3H, t, J=7Hz), 2.51 (3H, s), 4.37 (2H, q, J=7Hz), 7.21 (1H, s), 7.33 (4H, s), 7.72 (2H, d, J=5Hz), 8.85 (2H, d, J=5Hz)
Mass (m/z) : 339 (M$^+$)

(3) Ethyl 1-(2-fluorophenyl)-5-[4-(methylthio)phenyl]-3-carboxylate.
IR (Film) : 1725, 1600, 1510 cm$^{-1}$
NMR (CDCl$_3$, δ) : 1.39 (3H t J=7Hz) 2.42 (3H s) 4.42 (2H, q, J=7Hz), 6.9-7.6 (9H, m)

(4) Ethyl 1-(2,4-difluorophenyl)-5-[4-(methylthio)phenyl]pyrazole-3-carboxylate.
IR (Film) : 1720, 1605, 1515 cm$^{-1}$
NMR (CDCl$_3$, δ) : 1.40 (3H, t, J=7Hz), 2.42 (3H, s), 4.43 (2H, q, J=7Hz), 6.7-7.8 (8H, m)

(5) Ethyl 1-(3-fluorophenyl)-5-[4-(methylthio)phenyl]pyrazole-3-carboxylate.
IR (Film) : 1720 1605 1490 cm$^{-1}$
NMR (CDCl$_3$, δ) : 1.42 (3H, t, J=7Hz), 2.44 (3H, s), 4.42 (2H, q, J=7Hz), 6.9-7.5 (9H, m)

(6) Ethyl 5-[4-(methylthio)phenyl]-1-phenylpyrazole-3-carboxylate.
IR (Film) : 1705, 1600, 1560, 1500 cm$^{-1}$
NMR (CDCl$_3$, δ) : 1.40 (3H, t, J=7Hz), 2.45 (3H, s), 4.42 (2H, q, J=7Hz), 6.9-7.5 (10H, m)

(7) Ethyl 1-(4-methoxyphenyl)-5-[4-(methylthio)phenyl]pyrazole-3-carboxylate.
IR (Film) : 1720, 1605, 1510 cm$^{-1}$
NMR (CDCl$_3$, δ) : 1.42 (3H, t, J=7Hz), 2.47 (3H, s), 3.86 (3H, s), 4.45 (2H, q, J=7Hz), 6.8-7.4 (9H, m)

(8) Ethyl 1-(4-methylphenyl)-5-[4-(methylthio)phenyl]pyrazole-3-carboxylate.
IR Film) : 1720, 1605, 1520 cm$^{-1}$
NMR (CDCl$_3$, δ) : 1.42 (3H, t, J=7Hz), 2.37 (3H, s), 2.47 (3H, s), 4.45 (2H, q, J=7Hz), 7.00 (1H, s), 7.0-7.4 (8H, m)

(9) Ethyl 5-(4-fluorophenyl)-1-[4-[methylthio)phenyl]-pyrazole-3-carboxylate.
mp 95°-96.5° C.
IR (Nujol) 1710, 1610, 1545, 1495 cm$^{-1}$
NMR (CDCl$_3$, δ) : 1.42 (3H, t, J=7Hz), 2.49 (3H, s), 4.45 (2H, q, J=7Hz), 6.9-7.3 (9H, m)
Mass (m/z) : 356 (M$^+$)

(10) Ethyl 5-[4-(methylthio)phenyl]-1-(4-nitrophenyl)-pyrazole-3-carboxylate.
mp : 157°-159° C.
IR (Nujol) : 1695, 1655, 1590, 1510 cm$^{-1}$
Mass (m/z) : 383 (M$^+$)

(11) Ethyl 1-(4-fluorophenyl)-5-[5-(methylthio)-2-thienyl]pyrazole-3-carboxylate.
IR (Film) : 1720, 1600, 1510 cm$^{-1}$
NMR (CDCl$_3$, δ) : 1.39 (3H, t, J=7Hz), 2.44 (3H, s), 4.42 (2H, q, J=7Hz), 6.6-7.4 (7H, m)

(12) Ethyl 1-(4-fluorophenyl)-5-[4-(formylamino)-phenyl]pyrazole-3-carboxylate.
mp :184°-188° C.
IR (Nujol) : 3300, 1730, 1720, 1690, 1600, 1510 cm$^{-1}$
Mass (m/z) : 353 (M$^+$)

(13) Ethyl 5-[5-(methylthio)-2-thienyl]-1-(4-nitrophenyl)pyrazole-3-carboxylate.
IR (Film) : 1725, 1600, 1525, 1500 cm$^{-1}$

(14) Ethyl 1-(4-nitrophenyl)-5-(4-tolyl)pyrazole-3-carboxylate.
mp : 147°-149° C.
IR (Nujol) : 1715, 1595, 1525, 1500 cm$^{-1}$
NMR (CDCl$_3$, δ) : 1.43 (3H, t, J=7Hz), 2.39 (3H, s), 4.43 (2H, q, J=7Hz), 6.9-8.3 (9H, m)
Mass (m/z) : 351 (M$^+$)

(15) Ethyl 5-(4-methoxyphenyl)-1-(4-nitrophenyl)-pyrazole-3-carboxylate.
mp 161°-162° C.
IR (Nujol) : 1710, 1615, 1595, 1525, 1500 cm$^{-1}$
Mass (m/z) : 367 (M$^+$)

(16) Ethyl 5-(4-acetylphenyl)-1-(4-fluorophenyl)-pyrazole-3-carboxylate.
mp : 220°-222° C.
IR (Nujol) : 1710, 1610, 1510 cm$^{-1}$
Mass (m/z) : 352 (M$^+$)

(17) Ethyl 5-[3,5-di(t-butyl)-4-hydroxyphenyl]-1-(4-fluorophenyl)pyrazole-3-carboxylate.
mp : 173°-174° C.
IR (Nujol) : 3550, 1730, 1605, 1510 cm$^{-1}$
NMR (DMSO-$d_6$, δ) : 1.25 (18H, s), 1.31 (3H, t, J=8Hz), 4.32 (2H, q, J=8Hz), 6.96 (2H, s), 7.08 (1H, s), 7.2-7.5 (4H, m)
Mass (m/z) : 438 (M$^+$)

(18) Ethyl 1-(2,5-difluorophenyl)-5-[4-[methylthio)-phenyl]pyrazole-3-carboxylate.
mp : 81°-84° C.
IR (Nujol) : 1730, 1600, 1510 cm$^{-1}$
NMR (CDCl$_3$, δ) : 1.43 (3H, t, J=7Hz), 2.47 (3H, s), 4.46 (2H q, J=7Hz), 7.0-7.4 (8H, m)
Mass (m/z) : 374 (M$^+$)

(19) Ethyl 5-[4-(methylthio)phenyl]-1-(2-nitrophenyl)-pyrazole-3-carboxylate.
mp : 155°-157° C.
IR (Nujol) : 1715, 1605, 1535 cm$^{-1}$
NMR (CDCl$_3$, δ) : 1.41 (3H, t, J=7Hz), 2.45 (3H, s), 4.44 (2H, q, J=7Hz), 7.0-8.1 (9H m)
Mass (m/z) : 383 (M$^+$)

(20) Ethyl 1-(4-fluoro-2-nitrophenyl)-5-[4-(methylthio)phenyl]pyrazole-3-carboxylate.
IR (Film) : 1725, 1590, 1545, 1510 cm$^{-1}$
NMR (CDCl$_3$, δ) : 1.41 (3H, t, J=7Hz), 2.46 (3H, s), 4.36 (2H, q, J=7Hz), 6.9-8.0 (8H, m)
Mass (m/z) : 401 (M$^+$)

(21) 5-[4-(Methylthio)phenyl]-1-(4-nitrophenyl)-3-trifluoromethyl)pyrazole.
mp : 163°-164° C.
IR (Nujol) : 1600, 1525 cm$^{-1}$

(22) 3-(Fluoromethyl)-1-(4-fluorophenyl)-5-[4-methylthio)phenyl]pyrazole.
IR (Film) : 1600, 1515 cm$^{-1}$ NMR (CDCl₃, δ) : 2.44 (3H, s), 5.14 (1H, s), 5.67 (1H, s), 6.53 (1H, s), 6.8-7.3 (8H, m)
Mass (m/z) : 316 (M+)

(23) 3-(Fluoromethyl)-5-[4-(methylthio)phenyl]-1-(4-nitrophenyl)pyrazole.
mp : 165°-167° C.
IR (Nujol) : 1600, 1520, 1500 cm⁻¹
NMR (CDCl₃, δ) : 2.50 (3H, s), 5.36 (1H, s), 5.60 (1H, s), 6.64 (1H, s), 7.1-8.3 (8H, m)
Mass (m/z) : 343 (M+)

(24) 3-(Difluoromethyl)-1-(4-nitrophenyl)-5-[4-(methylthio)phenyl]pyrazole.
mp : 124°-129° C.
IR (Nujol) : 1600, 1520 cm⁻¹
NMR (CDCl₃, δ) : 2.50 (3H, s), 6.5-8.5 (10H, m)
Mass (m/z) : 361 (M+)

(25) 3-(Difluoromethyl)-1-(4-fluorophenyl)-5-[4-(methylthio)phenyl]pyrazole.
mp : 70°-71° C.
IR (Nujol) : 1600, 1520 cm⁻¹
NMR (CDCl₃, δ) : 2.48 (3H, s), 6.7-7.4 (10H, m)
Mass (m/z) : 334 (M+)

(26) Ethyl 1-(2-chlorophenyl)-5-[4-(methylthio)phenyl]pyrazole-3-carboxylate.
mp : 119°-120° C.
IR (Nujol) : 1715, 1605 cm⁻¹
NMR (CDCl₃, δ) : 1.42 (3H, t, J=7Hz), 2.45 (3H, s), 4.45 (2H, q, J=7Hz), 7.0-7.6 (9H, m)
Mass (m/z) : 372 (M+), 344

The following compounds (Examples 15-1) to 15-29)) were obtained according to a similar manner to that of Example 6.

EXAMPLE 15

(1) 1-(4-Fluorophenyl)-3-[4-(methylsulfonyl)phenyl]-pyrazole-5-carbonitrile.
mp : 200°-202° C.
IR (Nujol) : 2240, 1600, 1515 cm⁻¹
NMR (DMSO-d₆, δ) : 3.28 (3H, s), 7.4-8.3 (9H, m),
Mass (m/z) : 341 (M+)

(2) 1-(4-Fluorophenyl)-5-[4-(methylthio)phenyl]-pyrazole-3-carbonitrile.
mp : 106°-107° C.
IR (Nujol) : 2250, 1600, 1510 cm⁻¹
NMR (CDCl₃, δ) : 2.48 (3H, s), 6.84 (1H, s), 7.0-7.4 (8H, m)
Mass (m/z) : 309 (M+)

(3) 5-[4-(Methylsulfonyl)phenyl]-1-(4-pyridyl)pyrazole-3-carbonitrile.
mp : 194°-195° C.
IR (Nujol) : 2250, 1585, 1500 cm⁻¹
NMR (DMSO-d₆, δ) : 3.27 (3H, s), 7.3-8.1 (7H, m), 8.70 (2H, d, J=5Hz)
Mass (m/z) : 324 (M+)

(4) 5-[4-(Methylthio)phenyl]-1-(4-pyridyl)pyrazole-3-carbonitrile hydrochloride.
mp 185°-188° C.
IR (Nujol) : 2350, 2250, 2120, 2020, 1630, 1510 cm⁻¹
NMR (DMSO-d₆, δ) : 2.50 (3H, s), 7.1-7.6 (7H, m), 8 75 (2H, d, J=6Hz)
Mass [m/z] : 292 (M+)

(5) 1-[2-Fluorophenyl]-5-[4-(methylsulfonyl)phenyl]-pyrazole-3-carbonitrile.
mp : 147°-148° C.
IR (Nujol) : 2250, 1600, 1500 cm⁻¹
NMR (CDCl₃, δ) : 3.07 (3H, s), 7.00 (1H, s), 7.0-8.0 (8H, m)
Mass (m/z) : 341 (M+)

(6) 1-(2,4-Difluorophenyl)-5-[4-(methylsulfonyl)-phenyl]pyrazole-3-carbonitrile.
mp 129°-130° C.
IR (Nujol) : 2250, 1610, 1520 cm⁻¹
NMR (CDCl₃, δ) : 3.08 (3H, s), 6.8-8.0 (8H, m)
Mass (m/z) : 359 (M+)

(7) 1-(3-Fluorophenyl)-5-[4-(methylsulfonyl)phenyl]-pyrazole-3-carbonitrile.
mp : 167°-168° C.
IR (Nujol) : 2250, 1600, 1495 cm⁻¹
NMR (DMSO-d₆, δ) : 3.26 (3H, s), 7.2-8.0 (9H, m)
Mass (m/z) : 341 (M+)

(8) 5-(4-Methylsulfonyl)phenyl]-1-phenylpyrazole-3-carbonitrile.
m.p. : 179°-180° C.
IR (Nujol) : 2250, 1600, 1500 cm⁻¹
NMR (DMSO-d₆, δ) : 3.25 (3H, s) 7.3-8.0 (10H, m)
Mass (m/z) : 323 (M+)

(9) 1-(4-Methoxyphenyl)-5-[4-(methylsulfonyl)phenyl]-pyrazole-3-carbonitrile.
mp : 153°-154° C.
IR (Nujol) : 2250, 1600, 1515 cm⁻¹
NMR (DMSO-d₆, δ) : 3.25 (3H, s), 3.80 (3H, s), 7.0-8.0 (9H, m)
Mass (m/z) : 353 (M+)

(10) 1-(4-Methylphenyl)-5-[4-methylsulfonyl)phenyl]-pyrazole-3-carbonitrile.
mp : 210°-211° C.
IR (Nujol) : 2250, 1600, 1515 cm⁻¹
NMR (CDCl₃, δ) : 2.41 (3H, s), 3.08 (3H, s) 6.96 (1H, s), 7.1-8.0 (8H, m)

(11) 5-(4-Fluorophenyl)-1-[4-(methylthio)phenyl]-pyrazole-3-carbonitrile.
mp : 82°-83° C.
IR (Nujol) : 2250, 1610, 1545, 1500 cm⁻¹
Mass (m/z) : 309 (M+)

(12) 5-[4-Methylthio)phenyl]-1-(4-nitrophenyl)-pyrazole-3-carbonitrile.
mp : 165°-166° C.
IR (Nujol) : 2250, 1600, 1520, 1480 cm⁻¹
Mass (m/z) : 336 (M+)

(13) 1-(4-Fluorophenyl)-5-[5-(methylthio)-2-thienyl]-pyrazole-3-carbonitrile.
IR (Film) : 2250, 1600, 1510 cm⁻¹

(14) 5-[5-(Methylthio)-2-thienyl]-1-(4-nitrophenyl)-pyrazole-3-carbonitrile.
IR (Film) : 2250, 1600, 1525, 1500 cm⁻¹

(15) 1-(4-Fluorophenyl)-5-[4-(N-formylmethylamino)-phenyl]pyrazole-3-carbonitrile.
mp: 147°-148° C.
IR (Nujol) : 2250, 1675, 1615, 1510 cm⁻¹.
NMR (DMSO-d₆, δ) : 3.19 (3H, s), 7.2-7.7 (9H, m), 8.64 (1H, s)
Mass (m/z) : 320

(16) 5-[4-(Acetamido)phenyl]-1-(4-fluorophenyl)-pyrazole-3-carbonitrile.
mp: 96°-98° C.
IR (Nujol): 3340, 2250, 1670, 1600, 1535, 1510 cm⁻¹

NMR (DMSO-d₆, δ): 2.04 (3H, s), 7.1-7.6 (9H, m), 10.10 (1H, s)
Mass (m/z): 320 (M+)

17) 1-[4-(N-Formylmethylamino)phenyl]-5-(4-tolyl)-pyrazole-3-carbonitrile.
IR (Film): 2250, 1680, 1610, 1515 cm⁻¹
NMR (CDCl₃, δ): 2.38 (3H, s), 3.33 [3H, s), 6.8-7.4 (b 9H, m), 8.55 (1H, s)

18) 1-(4-Fluorophenyl)-5-(4-methoxyphenyl)pyrazole-3-carbonitrile.
mp: 122°-123° C.

IR (Nujol): 2250, 1610, 1500 cm$^{-1}$
NMR (CDCl$_3$, δ): 3.82 (3H, s), 6.8–7.4 (9H, m)
Mass (m/z): 293 (M+)

19) 5-(4-Methoxyphenyl)-1-(4-nitrophenyl)pyrazole-3-carbonitrile.
mp: 125°–126° C.
IR (Nujol): 2250, 1615, 1600, 1520, 1500 cm$^{-1}$
Mass (m/z): 320 (M+)

20) 1,5-Bis(4-methoxyphenyl)pyrazole-3-carbonitrile.
mp: 79°–80° C.
IR (Nujol): 2250, 1610, 1515 cm$^{-1}$
NMR (CDCl$_3$, δ): 3.81 (3H, s), 3.83 [3H, s), 6.7–7.3 (9H, m)
Mass (m/z): 305 (M+)

21) 5-(4-Cyanophenyl)-1-(4-fluorophenyl)pyrazole-3-carbonitrile.
mp: 154°–156° C.
IR (Nujol): 2250, 2230, 1615, 1510 cm$^{-1}$
NMR (CDCl$_3$, δ): 6.96 (1H, s), 7.0–7.7 (8H, m)
Mass (m/z): 288 (M+)

22) 5-[3,5-Di(t-butyl)-4-hydroxyphenyl]-1-(4-fluorophenyl)pyrazole-3-carbonitrile.
mp: 189°–190° C.
IR (Nujol): 3600, 2250, 1600, 1500 cm$^{-1}$
NMR (DMSO-d$_6$, δ): 1.24 (18H, s), 6.96 (2H, s), 7.3–7.5 (5H, m)
Mass (m/z): 391 (M+), 376

23) 1-(2-Fluorophenyl)-5-[4-(methylthio)phenyl]-pyrazole-3-carbonitrile.
mp: 76°–77° C.
IR (Nujol): 2250, 1600, 1505 cm$^{-1}$
NMR (CDCl$_3$, δ): 2.46 (3H, s), 6.87 (1H, s), 7.0—7.0 (8H, m)
Mass (m/z): 309 (M+)

24) 1-(2,4-Difluorophenyl)-5-[4-(methylthio)phenyl]-pyrazole-3-carbonitrile.
mp: 74°–75° C.
IR (Nujol): 2250, 1600, 1520 cm$^{-1}$
NMR (CDCl$_3$, δ): 2.47 (3H, s), 6.8–7.6 (8H, m)
Mass (m/z): 327 (M+)

25) 1-(2,5-Difluorophenyl)-5-[4-(methylthio)phenyl]-pyrazole-3-carbonitrile.
IR (Film): 2250, 1625, 1600, 1510 cm$^{-1}$ 26) 1-[4-(N-Formylmethylamino)phenyl]-5-[4-(methylthio)phenyl]pyrazole-3-carbonitrile.
mp: 132°–134° C.
IR (Nujol): 2250, 1670, 1600, 1515 cm$^{-1}$
Mass (m/z): 348 (M+)

27) 5-[4-(Methylthio)phenyl]-1-[2-nitrophenyl]-pyrazole-3-carbonitrile.
IR (Film): 2250, 1605, 1535 cm$^{-1}$ 28) 1-(4-Fluoro-2-nitrophenyl)-5-[4-(methylthio)phenyl]pyrazole-3-carbonitrile.
IR (Film): 2250, 1590, 1550, 1510 cm$^{-1}$ 29) 1-(2-Chlorophenyl)-5-[4-(methylthio)phenyl]-pyrazole-3-carbonitrile.
mp: 124°–125° C.
IR (Nujol): 2250, 1600 cm$^{-1}$
NMR (CDCl$_3$, δ): 2.45 (3H, s), 6.88 (1H, s), 7.0–7.5 (8H, m)
Mass (m/z): 325 (M+)

EXAMPLE 16

A mixture of 1-(4-fluorophenyl)-5-[4-(methylthio)phenyl]pyrazol-3-amine (3 g), cupric chloride (1.6 g) and t-butyl nitrite (1.14 g) in acetonitrile (50 ml) and dioxane (20 ml) was stirred at ambient temperature for 4 hours. The insoluble was filtered, and to the filtrate were added ethyl acetate and water. The organic layer was separated, washed with dilute hydrochloric acid, dried and concentrated. The oily residue (3.8 g) was purified by column chromatography on silica gel (40 g) eluting with a mixture of toluene and ethyl acetate (10:1) to give a brown oil of 1-(4-fluorophenyl)-5-[4-(methylthio)phenyl]-pyrazole (1.4 g).
IR (Film): 1600, 1510 cm$^{-1}$
NMR (CDCl$_3$, δ): 2.48 (3H, s), 6.48 (1H, d, J=1.8 Hz), 6.9–7.4 (8H, m), 7.70 (1H, d, J=1.8 Hz)
Mass (m/z): 284 (M+)

The following compounds (Examples 17-1) to 17-30)) were obtained according to a similar manner to that of Example 2.

EXAMPLE 17

1) 1-(4-Fluorophenyl)-5-[4-(methylsulfonyl)phenyl]-pyrazole.
mp: 110°–112° C.
IR (Nujol): 1600, 1515 cm$^{-1}$
NMR (DMSO-d$_6$, δ): 3.25 (3H, s), 6.83 (1H, d, J=1.9 Hz), 7.2–8.0 (9H, m)
Mass (m/z): 316 (M+)

2) 1-(4-Fluorophenyl)-5-[4-(methylsulfonyl)phenyl]-pyrazole-3-carbonitrile.
mp: 197° C.
IR (Nujol): 2240, 1600, 1515 cm$^{-1}$ 3) Ethyl 5-[4-(methylsulfonyl)phenyl]-1-(4-pyridyl)-pyrazole-3-carboxylate.
mp: 195°–199° C.
IR (Nujol): 1715, 1585, 1500 cm$^{-1}$
NMR (DMSO-d$_6$, δ): 1.33 (3H, t, J=7 Hz), 3.28 (3H, s), 4.37 (2H, q, J=7 Hz), 7.2–7.4 (3H, m), 7.62 (2H, d, J=8.5 Hz), 7.97 (2H, d, J=8.5 Hz), 8.68 (2H, broad s)
Mass (m/z): 371 (M+)

4) Ethyl 1-(2-fluorophenyl)-5-[4-[methylsulfonyl)-phenyl]pyrazole-3-carboxylate.
mp 165°–167° C.
IR (Nujol): 1725, 1600, 1500 cm$^{-1}$
NMR (CDCl$_3$, δ): 1.43 (3H, t, J=7 Hz), 3.06 (3H, s), 4.47 (2H, q, J=7 Hz), 7.0–7.9 (9H, m)
Mass (m/z): 388 (M+), 316

5) Ethyl 1-(2,4-difluorophenyl)-5-[4-(methylsulfonyl)phenyl]pyrazole-3-carboxylate.
mp: 184°–185° C.
IR (Nujol): 1730, 1605, 1520 cm$^{-1}$
NMR (CDCl$_3$, δ): 1.40 (3H, t, J=7 Hz), 3.07 (3H, s), 4.47 (2H, q, J=7 Hz), 6.8–8.0 (8H, m)
Mass (m/z): 406 (M+)

6) Ethyl 1-(3-fluorophenyl)-5-[4-(methylsulfonyl)phenyl]pyrazole-3-carboxylate.

mp: 110°–112° C.
IR (Nujol): 1720, 1605, 1490 cm$^{-1}$
NMR (CDCl$_3$, δ): 1.43 (3H, t, J=7 Hz), 3.09 (3H, s), 4.47 (2H, q, J=7 Hz), 7.0–8.1 (1H, m)
Mass (m/z): 388 (M+)

7) Ethyl 5-[4-(methylsulfonyl)phenyl]-1-phenyl-pyrazole-3-carboxylate.
IR (Film): 1720, 1600, 1500 cm$^{-1}$ 8) Ethyl 1-(4-methoxyphenyl)-5-[4-(methylsulfonyl)phenyl]pyrazole-3-carboxylate.
mp: 122°–125° C.
IR (Nujol): 1715, 1610, 1590, 1515 cm$^{-1}$
Mass (m/z): 400 (M+)

9) Ethyl 1-(4-methylphenyl)-5-[4-(methylsulfonyl)phenyl]pyrazole-3-carboxylate.
mp: 149°–151° C.
IR (Nujol): 1720, 1600, 1520 cm$^{-1}$
Mass (m/z): 384 (M+)

10) 5-[4-(Methylsulfonyl)phenyl]-1-(4-nitrophenyl)-pyrazole-3-carbonitrile.

11) 1-(4-Fluorophenyl)-5-[5-(methylsulfonyl)-2-thienyl]pyrazole-3-carbonitrile.
mp: 131°-132° C.
IR (Nujol): 2250, 1510 cm⁻¹
NMR (DMSO-d₆, δ): 3.35 (3H, s), 7.3-7.8 (7H, m)
Mass (m/z): 347 (H⁺)

12) 5-[5-(Methylsulfonyl)-2-thienyl]-1-(4-nitrophenyl)-pyrazole-3-carbonitrile.
mp: 98°-106° C.
IR (Nujol): 2250, 1615, 1595, 1530 cm⁻¹
Mass (m/z): 374 (M⁺)

13) 1-(2,5-Difluorophenyl)-5-[4-(methylsulfonyl)phenyl]pyrazole-3-carbonitrile.
mp: 139°-140° C.
IR (Nujol): 2250, 1620, 1605, 1505 cm⁻¹
NMR (DMSO-d₆, δ): 3.26 (3H, s), 7.4-8.0 (8H, m)
Mass (m/z): 359 (M⁺)

14) 1-[4-(N-Formylmethylamino)phenyl]-5-4-(methylsulfonyl)phenyl]pyrazole-3-carbonitrile.
mp: 170°-173° C.
IR (Nujol): 2250, 1610, 1520 cm⁻¹
NMR (DMSO-d₆, δ): 3.23 (3H, s), 3.26 (3H, s), 7.4-8.0 (9H, m), 8.68 (1H, s)
Mass (m/z): 380 (M⁺)

15) 5-[4-(Methylsulfonyl)phenyl]-1-(2-nitrophenyl)-pyrazole-3-carbonitrile.
mp: 123°-125° C.
IR (Nujol): 2250, 1605, 1535 cm⁻¹
Mass (m/z): 368 (M⁺)

16) 1-(4-Fluoro-2-nitrophenyl)-5-[4-(methylsulfonyl)phenyl]pyrazole-3-carbonitrile.
mp: 191°-193° C.
IR (Nujol): 2250, 1600, 1545, 1510 cm⁻¹
Mass (m/z): 386 (M⁺)

17) 5-[4-(Methylsulfonyl)phenyl]-1-(4-nitrophenyl)-3-(trifluoromethyl)pyrazole.
mp: 163°-164° C.
IR (Nujol): 1600, 1535 cm⁻¹
Mass (m/z): 411 (M⁺)

18) 3-Bromo-1-(4-fluorophenyl)-5-[4-(methylsulfonyl)phenyl]pyrazole.
mp: 185°-186° C.
IR (Nujol): 1600, 1515 cm⁻¹
NMR (DMSO-d₆, δ): 3.24 (3H, s), 7.03 (1H, s), 7.2-8.0 (8H, m)
Mass (m/z): 396, 394

19) N-Cyclopropyl-1-(4-fluorophenyl)-5-[4-(methylsulfonyl)phenyl]pyrazole-3-carboxamide.
mp: 185°-186° C.
IR (Nujol): 3350, 1660, 1605, 1545, 1535, 1510 cm⁻¹
NMR (CDCl₃, δ): 0.6-1.0 (4H, m), 2.8-3.0 (1H, m), 3.08 (3H, s), 7.0-7.5 (8H, m), 7.90 (2H, d, J=8 Hz)
Mass (m/z): 399 (M⁺)

20) Ethyl 5-[4-(methylsulfonyl)phenyl]-1-[4-nitrophenyl]pyrazole-3-carboxylate.
mp: 209°-210° C.
IR (Nujol): 1710, 1600, 1525 cm⁻¹
NMR (DMSO-d6, δ): 1.33 (3H, t, J=7Hz), 3.26 (3H, s), 4.37 (2H, q, J=7 Hz), 7.36 (1, s), 7.5-8.4 (8H, m)
Mass (m/z): 415 (M⁺)

21) 3-(Fluoromethyl)-1-(4-fluorophenyl)-5-[4-(methylsulfonyl)phenyl]pyrazole.
mp: 166°-167° C.
IR (Nujol): 1600, 1515 cm⁻¹
NMR (DMSO-d₆, δ): 3.25 (3H, s), 5.35 (1H, s), 5.59 (1H, s), 6.9-8.0 (8H, m)
Mass (m/z): 348

22) 1-(4-Fluorophenyl)-5-[4-(methylsulfonyl)phenyl]-3-pyrazolylmethyl acetate.
mp: 102°-103° C.
IR (Nujol): 1740, 1720, 1600, 1515 cm⁻¹
NMR (CDCl₃, δ): 2.14 (3H, s), 3.07 (3H, s), 5.10 (2H, s), 6.66 (1H, s), 7.0-8.0 (8H, m)
Mass (m/z): 388 (M⁺), 345

23) 3-(Chloromethyl)-1-(4-fluorophenyl)-5-[4-(methylsulfonyl)phenyl]pyrazole.
mp: 155°-156° C.
IR (Nujol): 1600, 1515 cm⁻¹
NMR (DMSO-d₆, δ): 3.25 (3H, s), 4.82 (2H, s), 6.91 (1H, s), 7.2-8.0 (8H, m)
Mass (m/z): 364 (M⁺)

24) 3-(Fluoromethyl)-5-[4-(methylsulfonyl)phenyl]-1-(4-nitrophenyl)pyrazole.
mp: 152°-153° C.
IR (Nujol): 1600, 1525 cm⁻¹
Mass (m/z): 375 (M⁺)

25) 3-(Difluoromethyl)-1-[4-(metylamino)phenyl]-5-[4-(methylsulfonyl)phenyl]pyrazole.
mp: 175°-176° C.
IR (Nujol): 3430, 1615, 1540 cm⁻¹
NMR (CDCl₃, δ): 2.72 (3H, s), 3.07 (3H, s), 3.97 (1H, s), 6.5-8.1 (10H, m)
Mass (m/z): 377 (M⁺)

26) 3-(Difluoromethyl)-1-(4-fluorophenyl)-5-[4-(methylsulfonyl)phenyl]pyrazole.
mp 190°-191° C.
IR (Nujol): 1600, 1515 cm⁻¹
NMR (CDCl₃, δ): 3.08 (3H, s), 6.5-8.0 (10H, m)
Mass (m/z): 366 (M⁺)

27) 4-Bromo-1-(4-fluorophenyl)-5-[4-(methylsulfonyl)phenyl]pyrazole.
mp 169°-170° C.
IR (Nujol): 1600, 1510 cm⁻¹
NMR (CDCl₃, δ) 3.10 (3H, s), 7.0-8.0 (9H, m)
Mass (m/z): 396, 394

28) N-Phenyl-1-(4-fluorophenyl)-5-[4-(methylsulfonyl)phenyl]pyrazole-3-carboxamide.
mp: 232°-233° C.
IR (Nujol): 3350, 1680, 1595, 1535, 1505 cm⁻¹
NMR (DMSO-d₆, δ): 3.26 (3H, s), 7.0°-8.0 (14H, m), 10.26 (1H, s)
Mass (m/z): 435

29) 1-(4-Fluorophenyl)-5-[4-(methylsulfonyl)phenyl]-3-(1-pyrrolidinylcarbonyl)pyrazole.
mp: 229°-230° C.
IR (Nujol): 1615, 1515, 1500 cm⁻¹
NMR (CDCl₃, δ): 1.77-2.07 (4H, m), 3.00 (3H, s), 3.67 (2H, t, J=6 Hz), 3.97 (2H, t, J=6 Hz), 6.9-7.5 (7H, m), 7.87 (2H, d, J=8 Hz)
Mass (m/z): 413 (M⁺)

30) 1-(2-Chlorophenyl)-5-[4-(methylsulfonyl)phenyl]-pyrazole-3-carbonitrile.
mp: 151°-152° C.
IR (Nujol): 2250, 1610, 1545, 1490 cm⁻¹
NMR (CDCl₃, δ): 3.05 (3H, s), 7.02 (1H, s), 7.3-8.0 (8H, m)
Mass (m/z): 357 (M⁺)

EXAMPLE 18

A mixture of ethyl 1-(4-fluorophenyl)-5-[4-(methylthio)phenyl]pyrazole-3-carboxylate (3.6 g) and potassium hydroxide (2 g) in methanol (50 ml) was refluxed for 30 minutes. The solvent was evaporated. The residue was dissolved in water and washed with chloroform. The aqueous layer was acidified with dilute hydrochloric acid and extracted with ethyl acetate. The extract was washed with water, dried over magnesium sulfate, and concentrated. The residue obtained was recrystallized from ethanol to give crystals of 1-(4-fluorophenyl)-5-[4-(methylthio)phenyl]pyrazole-3-carboxylic acid (2 g).

mp: 199°-200° C.
IR Nujol): 3550, 3300, 2500, 1710, 1680, 1600, 1515 cm$^{-1}$
Mass (m/z): 328 (H$^+$)

The following compounds (Examples 19-1) to 19-11)) were obtained according to a similar manner to that of Example 18.

EXAMPLE 19

1) 5-[4-(Methylsulfonyl)phenyl]-1-(4-pyridyl)pyrazole-3-carboxylic acid.
mp: 270°-271° C. (dec.)
IR (Nujol): 1690, 1610, 1510 cm$^{-1}$
NMR (DMSO-d$_6$, δ): 3.28 (3H, s), 7.2-8.0 (7H, m), 8.66 (2H, broad s), 13.25 (1H, s)
Mass (m/z): 343 (M$^+$)

2) 5-[4-(Methylthio)phenyl]-1-(4-pyridyl)pyrazole-3-carboxylic acid.
mp: 225°-227° C.
IR (Nujol): 3400, 2400, 1700, 1600, 1510 cm$^{-1}$
Mass (m/z): 311 (M$^+$)

1-(2-Fluorophenyl)-5-[4-(methylsulfonyl)phenyl]pyrazole-3-carboxylic acid.
mp: 228°-229° C. (dec.)
IR (Nujol): 2600, 1700, 1600, 1500 cm$^{-1}$
NMR (DMSO-d$_6$, δ): 3.25 (3H, s), 7.22 (1H, s), 7.3-8.0 (8H, m), 13.17 (1H, s)
Mass (m/z): 360 (M$^+$)

4) 1-(2,4-Difluorophenyl)-5-[4-(methylsulfonyl)phenyl]pyrazole-3-carboxylic acid.
mp: 231°-233° C. (dec.)
IR (Nujol): 2600, 1700, 1600, 1515 cm$^{-1}$
NMR (DMSO-d$_6$, δ) 3.25 (3H, s), 7.3-8.0 (8H, m), 13.20 (1H, s)
Mass (m/z): 378 (M$^+$)

5) 1-(3-Fluorophenyl)-5-[4-(methylsulfonyl)phenyl]pyrazole-3-carboxylic acid.
IR (Nujol): 2630, 1705, 1600, 1490 cm$^{-1}$
NMR (DMSO-d$_6$, δ): 3.26 (3H, s), 7.1-8.0 (9H, m)
Mass (m/z): 360 (M$^+$)

(6) 5-[4-(Methylsulfonyl)phenyl]-1-phenylpyrazole-3-carboxylic acid.
mp : 203°-205° C.
IR (Nujol): 2625, 1700, 1600, 1495 cm$^{-1}$
Mass (m/z) : 342 (M$^+$)

(7) 1-(4-Methoxyphenyl)-5-[4-methylsulfonyl)phenyl]pyrazole-3-carboxylic acid.
mp : 197°-199° C.
IR (Nujol) : 1700, 1600, 1515 cm$^{-1}$
Mass (m/z) : 372 (M$^+$)

(8) 1-(4-Methylphenyl)-5-[4-(methylsulfonyl)phenyl]pyrazole-3-carboxylic acid.
mp : 185°-187° C.
IR (Nujol) : 2600, 1700, 1600, 1510 cm$^{-1}$
Mass (m/z) : 356 (M$^+$)

(9) 5-(4-Fluorophenyl)-1-[4-(methylthio)phenyl]pyrazole-3-carboxylic acid.
mp 176°-178° C.
IR (Nujol) : 3500, 1680, 1610, 1545, 1490 cm$^{-1}$
Mass (m/z) 328 (M$^+$)

(10) 5-[4-(Methylthio)phenyl]-1-(4-nitrophenyl)pyrazole-3-carboxylic acid.
mp : 188°-189° C.
IR (Nujol) : 1690, 1595, 1520 cm$^{-1}$
Mass (m/z) 355 (M$^+$)

(11) 1-(2,4-Difluorophenyl)-5-[4-(methylthio)phenyl]pyrazole-3-carboxylic acid
mp : 188°-190° C.
IR (Nujol) : 3300, 2500, 1705, 1680, 1600, 1520 cm$^{-1}$
Mass (m/z) : 346 (M$^+$)

EXAMPLE 20

A mixture of ethyl 1-(4-methoxyphenyl)-5-[4-(methylsulfonyl)phenyl]pyrazole-3-carboxylate (2 g) and hydriodic acid (57%, 5 ml) in acetic acid (10 ml) was refluxed for 5 hours. The reaction mixture was concentrated and the residue was triturated in an aqueous solution of sodium bisulfite giving a powder. This crude powder was purified by column chromatography on silica gel (80 g) eluting with a mixture of chloroform and methanol to give a powder of 1-(4-hydroxyphenyl)-5-[4-(methylsulfonyl)phenyl]pyrazole-3-carboxylic acid (0.86 g).
mp : 233°-236° C. (dec.)
IR (Nujol) : 3550, 3250, 1700, 1600, 1515 cm$^{-1}$
Mass (m/z) : 358 (M$^+$)

EXAMPLE 21

A mixture of 1-(4-fluorophenyl)-5-[4-(methylthio)phenyl]pyrazole-3-carboxylic acid (13.5 g) and thionyl chloride (10 ml) in dichloroethane (30 ml) was refluxed for 1 hour. The mixture was concentrated to give an oil of 1-(4-fluorophenyl)-5-[4-(methylthio)phenyl]pyrazole-3-carbonyl chloride.
IR (Film) : 1760, 1605, 1510 cm$^{-1}$ A solution of the above chloride in tetrahydrofuran (50 ml) was added dropwise to a mixture of 28% ammonia water and tetrahydrofuran (50 ml) at 5° to 10° C. The mixture was stirred for 1 hour at ambient temperature. The solvent was evaporated and the residue was triturated with water to give crystals of 1-(4-fluorophenyl)-5-[4-(methylthio)phenyl]pyrazole-3-carboxamide (11.2 g).
mp .180°-181° C.
IR (Nujol) : 3500, 3425, 1670, 1600, 1510 cm$^{-1}$
NMR (CDCl$_3$, δ) : 2.48 (3H, s), 5.70 (1H, s), 6.87 (1H, s), 7.0-7.4 (9H, m)
Mass (m/z) : 327 (M$^+$)

The following compounds (Examples 22-1) to 22-13)) were obtained according to a similar manner to that of Example 21.

EXAMPLE 22

(1) 5-[4-(Methylsulfonyl)phenyl]-1-(4-pyridyl)pyrazole-3-carboxamide.
mp : 286°-288° C.
IR (Nujol) : 3550, 3300, 3200, 1690, 1595, 1500 cm$^{-1}$
NMR (DMSO-d$_6$, δ) : 3.28 (3H, s), 7.18 (1H, s), 7.3-8.0 (8H, m), 8.66 (2H, d, J=5Hz)
Mass (m/z) : 342 (M$^+$)

(2) 5-[4-(Methylthio)phenyl]-1-(4-pyridyl)pyrazole-3-carboxamide.
mp 213°-215° C.
IR (Nujol) : 3360, 3150, 1680, 1595 cm$^{-1}$ (3) 1-(2-Fluorophenyl)-5-[4-(methylsulfonyl)phenyl]pyrazole-3-carboxamide.
mp 198°-199° C.
IR (Nujol) : 3500, 3150, 1690, 1600, 1510 cm$^{-1}$
NMR (CDCl$_3$, δ) : 3.06 (3H, s), 5.68 (1H, s), 6.86 (1H, s), 7.1-7.9 (9H, m)
Mass (m/z) : 359 (M$^+$)

(4) 1-(2,4-Difluorophenyl)-5-[4-(methylsulfonyl)phenyl]pyrazole-3-carboxamide.
mp : 213°-214° C.

IR (Nujol) : 3440, 3150, 1685, 1610, 1520 cm$^{-1}$
NMR (DMSO-d$_6$, δ) : 3.25 (3H, s), 7.23 (1H, s), 7.3–8.0 (7H, m)
Mass (m/z) : 377 (M$^+$)

(5) 1-(3-Fluorophenyl)-5-[4-(methylsulfonyl)phenyl]-pyrazole-3-carboxamide.
mp : 217°–218° C.
IR (Nujol) : 3460, 3220, 1680, 1600, 1490 cm$^{-1}$
NMR (DMSO-d$_6$, δ) : 3.26 (3H, s), 7.1–8.0 (11H, m)
Mass (m/z) : 359 (M$^+$)

(6) 5-[4-(Methylsulfonyl)phenyl]-1-phenylpyrazole-3-carboxamide.
mp : 265°–266° C.
IR (Nujol) : 3475, 3200, 1680, 1600, 1495 cm-1
NMR (DMSO-d$_6$, δ) : 3.24 (3H, s), 7.16 (1H, s), 7.3–8.0 (11H, m)
Mass (m/z) : 341 (M$^+$)

(7) 1-(4-Methoxyphenyl)-5-[4-{methylsulfonyl)phenyl]-pyrazole-3-carboxamide.
mp 178°–179° C.
IR (Nujol) : 3480, 3310, 3230, 1675, 1590, 1515 cm$^{-1}$
NMR (DMSO-d$_6$, δ) : 3.24 (3H, s), 3.79 (3H, s), 6.9–8.0 (11H, m)
Mass (m/z) : 371 (M$^+$)

(8) 1-(4-Hydroxyphenyl)-5-[4-(methylsulfonyl)phenyl]-pyrazole-3-carboxamide.
mp : 269°–271° C.
IR (Nujol) : 3550, 3460, 3200, 1680, 1600, 1520 cm$^{-1}$
Mass (m/z) : 357 (M$^+$)

(9) 1-Methylphenyl)-5-[4-(methylsulfonyl)phenyl]-pyrazole-3-carboxamide.
mp 125°–130° C.
IR (Nujol) : 3470, 3200, 1680, 1600, 1515 cm$^{-1}$
NMR [DMSO-d$_6$, δ) : 2.35 (3H, s), 3.24 (3H, s), 7.1–8.0 (11H, m)
Mass (m/z) : 355 (M$^+$)

(10) 5-4-Fluorophenyl)-1-[4-(methylthio)phenyl]-pyrazole-3-carboxamide.
mp 157°–159° C.
IR (Nujol) : 3460, 3270, 1670, 1610, 1595, 1545, 1495 cm$^{-1}$
Mass (m/z) : 327 (M$^+$)

(11) 5-[4-(Methylthio)phenyl]-1-(4-nitrophenyl)-pyrazole-3-carboxamide.
mp 192°–194° C.
IR (Nujol) 3480, 3150, 1690, 1610, 1595, 1520 cm$^{-1}$
Mass (m/z) : 354 (M$^+$)

(12) 1-(4-Fluorophenyl)-5-(4-tolyl)pyrazole-3-carboxamide
mp : 183°–186° C.
IR (Nujol) : 3500, 3350, 3300, 1685, 1610, 1510 cm$^{-1}$
NMR (DMSO-d$_6$, δ) : 2.29 (3H, s), 6.8–7.5 (9H, m), 7.68 (2H, s)
Mass (m/z) : 295 (M$^+$)

(13) 1-(2,4-Difluorophenyl)-5-[4-(methylthio)phenyl]-pyrazole-3-carboxamide.
mp : 171°–173° C.
IR {Nujol) : 3440, 3200, 1665, 1600, 1515 cm$^{-1}$
Mass (m/z) : 345 (M$^+$)

EXAMPLE 23

A mixture of 1-(4-hydroxyphenyl)-5-[4-(methylsulfonyl)phenyl]pyrazole-3-carboxamide (1.3 g) and methanesulfonyl chloride (2.5 g) in pyridine (20 ml) was stirred at 50° C. for 5 hours. The solvent was evaporated, and dilute hydrochloric acid and ethyl acetate was added to the residue. The organic layer was washed with water, dried and concentrated. The residue was purified by column chromatography on silica gel (20 g) eluting with a mixture of chloroform and methanol (20:1) to give crystals of 5-[4-(methylsulfonyl)phenyl]-1-[4-(methylsulfonyloxy)-phenyl]-pyrazole-3-carbonitrile (0.79 g).
mp 195°–196° C.
IR (Nujol) : 2250, 1600, 1510 cm$^{-1}$
NMR (DMSO-d$_6$, δ) : 3.10 (3H, s), 3.45 (3H, s), 7.4–8.0 (9H, m)
Mass (m/z) : 417 (M$^+$)

EXAMPLE 24

A solution of sodium periodate (0.7 g) in water (5 ml) was added to an ice-cooled solution of 1-(4-fluorophenyl)-5-[4-(methylthio)phenyl]pyrazole-3-carbonitrile (0.6 g) in methanol (50 ml). The resulting solution was stirred at room temperature for 8 hours. The insoluble was filtered off and the filtrate was concentrated. The residue obtained was dissolved in ethyl acetate, and washed with an aqueous solution of sodium hydrogen sulfite and water. The organic layer was dried and concentrated to give an oily residue (0.6 g). The residue was purified by column chromatography on silica gel (13 g) eluting with a mixture of chloroform and methanol (50:1). The purified product was crystallized from a mixture of hexane and ethanol to give crystals of 1-(4-fluorophenyl)-5-[4-(methylsulfinyl)phenyl]pyrazole-3-carbonitrile (0.45 g).
mp 104°–105° C.
IR (Nujol) 2250, 1600, 1515 cm$^{-1}$
NMR (CDCl$_3$, δ) : 2.76 (3H, s), 6.94 (1H, s), 7.0–7.7 (8H, m)
Mass (m/z) : 325 (M$^+$), 310

EXAMPLE 25

A mixture of 5-(4-fluorophenyl)-1-[4-(methylthio)phenyl]pyrazole-3-carbonitrile (0.75 g) and 30% hydrogen peroxide solution (1.4 ml) in acetic acid (10 ml) was stirred at 50° C. for 4 hours. The reaction mixture was concentrated, and the residue was recrystallized from ethanol to give crystals of 5-(4-fluorophenyl)-1-[4-(methylsulfonyl)phenyl]pyrazole-3-carbonitrile (0.66 g).
mp : 162°–163° C.
IR (Nujol) : 3140, 2250, 1610, 1595, 1500 cm$^{-1}$
NMR (CDCl$_3$, δ) : 3.09 (3H, s), 6.89 (1H, s), 7.0–8.0 (8H, m)
Mass (m/z) : 341 (M$^+$)

EXAMPLE 26

A mixture of 5-[4-(methylsulfonyl)phenyl]-1-(4-nitrophenyl)pyrazole-3-carbonitrile (1.1 g), iron powder (1.1 g) and ammonium chloride (0.11 g) in ethanol (20 ml) and water (7 ml) was refluxed for 1 hour. The solvent was evaporated, and the residue was filtered, washed with water and dissolved in hot ethyl acetate. The solution was filtered and the filtrate was concentrated. The residue obtained was recrystallized from ethyl acetate to give crystals of 1-(4-aminophenyl)-5-[4-(methylsulfonyl)phenyl]pyrazole-3-carbonitrile (0.83 g).
mp : 228°–229° C.
IR (Nujol) : 3480, 3400, 3150, 2250, 1645, 1605, 1520 cm$^{-1}$
NMR (DMSO-d$_6$, δ) : 3.25 (3H, s), 5.57 (2H, s), 6.5–8.0 (9H, m)
Mass (m/z) : 338 (M$^+$)

EXAMPLE 27

A mixture of 1-(4-fluorophenyl)-5-[4-(methylsulfonyl)phenyl]pyrazol-3-amine (0.7 g) and acetic anhydride (0.22 ml) in dichloromethane (15 ml) was stirred at ambient temperature for 3 hours, and concentrated. The residue was purified by column chromatography on silica gel (15 g) eluting with a mixture of toluene and ethyl acetate (2:1). The desired product (0.63 g) was recrystallized from ethanol to give pale brown crystals of N-{1-(4-fluorophenyl)-5-[4-(methylsulfonyl)phenyl]-3-pyrazolyl}acetamide (0.52 g).

mp : 203°-205° C.
IR (Nujol) : 3350, 1690, 1580, 1510 cm$^{-1}$
NMR (DMSO-d$_6$, δ) : 2.05 (3H, s), 3.21 (3H, s), 6.98 (1H, s), 7.2-7.6 (6H, m), 7.89 (2H, d, J=8Hz), 10.72 (1H, s)
Mass (m/z) 373 (M+), 331

EXAMPLE 28

Methyl chloroformate (0.163 ml) in acetonitrile (0.7 ml) was added dropwise to a stirred solution of 1-(4-fluorophenyl)-5-[4-(methylsulfonyl)phenyl]pyrazole-3-amine (0.7 g) and pyridine (0.171 ml) in acetonitrile (6 ml) and tetrahydrofuran (7 ml) at −20° C. The mixture was stirred at 5° C. for 1 hour, diluted with ethyl acetate, washed with water, dried, and concentrated. The residue (0.9 g) was recrystallized from a mixture of chloroform and ethanol to give pale brown crystals of methyl N-{1-(4-fluorophenyl)-5-[4-(methylsulfonyl)phenyl]-3-pyrazolyl}carbamate (0.51 g).

mp 225°-227° C.
IR (Nujol) : 3320, 1730, 1585, 1510 cm$^{-1}$
NMR (DMSO-d$_6$, δ) : 3.16 (3H, s), 3.62 (3H, s), 6.73 (1H, s), 7.1-7.5 (6H, m), 7.84 (2H, d, J=8Hz), 10.22 (1H, s)
Mass (m/z) : 389 (M+), 357

EXAMPLE 29

A mixture of 1-(4-fluorophenyl)-5-[4-(methylsulfonyl)phenyl]pyrazol-3-amine (0.8 g) and methanesulfonyl chloride (0.224 ml) in pyridine (8 ml) was stirred at ambient temperature for 2 hours. Pyridine was evaporated, and the residue was dissolved in ethyl acetate, washed with water and dilute hydrochloric acid, dried, and concentrated. The residual oil (1.1 g) was purified by column chromatography on silica gel (20 g) eluting with a mixture of toluene and ethyl acetate (2:1). The product (0.74 g) was recrystallized from ethanol to give pale brown crystals of N-{1-(4-fluorophenyl)-5-[4-(methylsulfonyl)phenyl]-3-pyrazolyl}methanesulfonamide (0.62 g).

mp : 186°-187° C.
IR (Nujol) : 3150, 1555, 1520 cm$^{-1}$
NMR (DMOS-d$_6$, δ) : 3.17 (3H, s), 3.24 (3H, s), 6.55 (1H, s), 7.2-7.6 (6H, m), 7.91 (2H, d, J=8.5Hz), 10.37 (1H, s)
Mass (m/z) : 409 (M+)

EXAMPLE 30

A mixture of 1-(4-aminophenyl)-5-[4-(methylsulfonyl)phenyl]pyrazole-3-carbonitrile (0.7 g) and formic acid (1 ml) in formalin (37%; 5 ml) was refluxed for 30 minutes. Chloroform was added, and the mixture was washed with water, dried, and concentrated. The residual oil was purified by column chromatography on silica gel eluting with a mixture of ethyl acetate and toluene (2:1). The product obtained was recrystallized from ethyl acetate to give crystals of 1-[4-(dimethylamino)phenyl]-5-[4-(methylsulfonyl)phenyl]-pyrazole-3-carbonitrile (0.46 g).

mp : 171°-172° C.
IR (Nujol) : 2240, 1610, 1530 cm$^{-1}$
Mass (m/z) : 366 (M+)

EXAMPLE 31

A mixture of 1-(4-aminophenyl)-5-[4-(methylsulfonyl)phenyl]pyrazole-3-carbonitrile (1 g), methyl iodide (0.42 g) and potassium carbonate (0.6 g) in N,N-dimethylformamide (10 ml) was stirred at ambient temperature for 1 hour. The mixture was poured into water and extracted with ethyl acetate. The extract was washed with water, dried, and concentrated. The residue (1.2 g) was purified by column chromatography on silica gel (20 g) eluting with chloroform to give crystals of 1-[4-(methylamino)phenyl]-5-[4-(methylsulfonyl)phenyl]pyrazole-3 -carbonitrile (0.31 g).

mp : 166°-168° C.
IR (Nujol) : 3450, 2240, 1610, 1530 cm$^{-1}$
NMR (DMSO-d$_6$, δ) : 251 (3H, d, J=5Hz), 3.25 (3H, s), 6.17 (1H, q, J=5Hz), 6.5-8.0 (9H, m)

The following compound (Example 32) was obtained according to a similar manner to that of Example 10.

EXAMPLE 32

1-(4-Fluorophenyl)-5-[4-methylthio)phenyl]pyrazol-3-ylmethylamine.

IR (Film) : 3400, 3300, 1600, 1500 cm$^{-1}$
NMR (CDCl$_3$, δ) : 1.85 (2H, s) 2.47 (3H, s), 3.96 (2H, s), 6.43 (1H, s) 7.0-7.4 (8H, m)
Mass (m/z) : 313 (M$^{30}$)

The following compounds (Examples 33-1) to 33-7)) were obtained according to a similar manner to that of Example 24.

EXAMPLE 33

(1) 1-(2-Fluorophenyl)-5-[4-(methylsulfinyl)phenyl]-pyrazole-3-carbonitrile.
mp : 139°-140° C.
IR (Nujol) : 2250, 1600, 1500 cm$^{-1}$
NMR (CDCl$_3$, δ) : 2.73 (3H, s), 6.96 (1H, s), 7.0-7.7 (8H, m)
Mass (m/z) : 325 (M+), 310

(2) 1-(2,4-Difluorophenyl)-5-[4-(methylsulfinyl)-phenyl]pyrazole-3-carbonitrile.
mp : 136°-137° C.
IR (Nujol) : 2260, 1615, 1520 cm$^{-1}$
NMR (CDCl$_3$, δ) : 2.74 (3H, s), 6.8-7.7 (8H, m)
Mass (m/z) : 343 (M+), 328

(3) 1-[4-(N-Formylmethylamino)phenyl]-5-[4-(methylsulfinyl)phenyl]pyrazole-3-carbonitrile.
IR (Film) : 2250, 1680, 1610, 1515 cm$^{-1}$ (4) 5-[4-(Methylsulfinyl)phenyl]-1-(4-nitrophenyl)-3-(trifluoromethyl)pyrazole.
mp : 167°-168° C.
IR (Nujol) : 1600, 1530, 1495 cm$^{-1}$
Mass (m/z) : 395 (M+)

(5) 3-(Fluoromethyl)-1-(4-fluorophenyl)-5-[4-methylsulfinyl)phenyl]pyrazole.
mp 130°-131° C.
IR (Nujol) : 1600, 1515 cm$^{-1}$
NMR (CDCl$_3$, δ) : 2.75 (3H, s), 5.36 (1H, s), 5.60 (1H, s), 6.69 (1H, s), 7.0-7.7 (8H, m)
Mass (m/z) : 332 (M+)

(6) 3-(Chloromethyl)-1-(4-fluorophenyl)-5-[4-(methylsulfinyl)phenyl]pyrazole.
mp 96°-97° C.
IR (Nujol) : 1600, 1515 cm$^{-1}$
NMR (CDCl$_3$, δ) : 2.75 (3H, s), 4.70 (2H, s), 6.65 (1H, s), 7.0-7.7 (8H, m)
Mass (m/z) : 348 (M+)

(7) 3-(Difluoromethyl)-1-(4-fluorophenyl)-5-[4-(methylsulfinyl)phenyl]pyrazole.
mp : 165°–166° C.
IR (Nujol) : 1600, 1515 cm$^{-1}$
NMR (CDCl$_3$, δ) : 2.75 (3H, s), 6.5–7.7 (10H, m)
Mass (m/z) : 350 (M$^+$), 335

The following compounds (Examples 34-1) to 34-13)) were obtained according to a similar manner to that of Example 26.

EXAMPLE 34

(1) 1-(4-Aminophenyl)-5-[5-(methylsulfonyl)-2-thienyl]pyrazole-3-carbonitrile.
mp : 200°–203° C.
IR (Nujol) : 3500, 3420, 2250, 1620, 1520 cm$^{-1}$
Mass (m/z) : 344 (M$^+$)

(2) Ethyl 1-(4-aminophenyl)-5-(4-tolyl)pyrazole-3-carboxylate.
mp : 174°–175° C.
IR (Nujol) : 3460, 3380, 1730, 1700, 1635, 1520 cm$^{-1}$
Mass (m/z) : 321 (M$^+$)

(3) 1-(4-Aminophenyl)-1-(4-methoxyphenyl)pyrazole-3-carbonitrile
mp : 175°–177° C.
IR (Nujol) : 3420, 3350, 2250, 1640, 1610, 1520 cm$^{-1}$
Mass (m/z) : 290 (M$^+$)

(4) Ethyl 1-(4-aminophenyl)-5-[4-(methylthio)phenyl]pyrazole-3-carboxylate.
mp : 153°–155° C.
IR (Nujol) : 3450, 3350, 3230, 1715, 1635, 1610, 1520 cm$^{-1}$
Mass (m/z) : 353 (M$^+$)

(5) 1-(2-Aminophenyl)-5-[4-(methylsulfonyl)phenyl]pyrazole-3-carbonitrile.
mp : 191°–192° C.
IR (Nujol) : 3500, 3400, 2250, 1635, 1600, 1500 cm$^{-1}$
Mass (m/z) : 338 (M$^+$)

(6) 1-(2-Amino-4-fluorophenyl)-5-[4-(methylsulfonyl)phenyl]pyrazole-3-carbonitrile.
mp : 206°–208° C.
IR (Nujol) : 3500, 3400, 2250, 1630, 1510 cm$^{-1}$
Mass (m/z) : 356 (M$^+$)

(7) 1-(4-Aminophenyl)-5-[4-(methylthio)phenyl]-3-(trifluoromethyl)pyrazole.
mp : 112°–113° C.
IR (Nujol) : 3500, 3400, 1625, 1600, 1520, 1500 cm$^{-1}$
Mass (m/z) : 349 (M$^+$)

(8) 1-(4-Aminophenyl)-5-[4-(methylsulfonyl)phenyl]-3-(trifluoromethyl)pyrazole.
mp : 250°–251° C.
IR (Nujol) : 3500, 3400, 1640, 1600, 1520, 1500 cm$^{-1}$
Mass (m/z) : 381 (M$^+$)

(9) 1-(4-Aminophenyl)-5-[4-(methylsulfinyl)phenyl]-3-(trifluoromethyl)pyrazole.
mp : 213°–214° C.
IR (Nujol) : 3500, 3380, 3250, 1645, 1610, 1525, 1505 cm$^{-1}$
Mass (m/z) : 365 (M$^+$)

(10) 1-(4-Aminophenyl)-3-(methylsulfonyl)-5-[4-methylsulfonyl)phenyl]pyrazole.
mp 208°–210° C.
IR (Nujol) : 3500, 3400, 1635, 1605, 1520 cm$^{-1}$
Mass (m/z) : 391 (M$^+$)

(11) 1-(4-Aminophenyl)-3-(fluoromethyl)-5-[4(methylsulfonyl)phenyl]pyrazole.
mp 112°–116° C.
IR (Nujol) : 3420, 3240, 1610, 1520 cm$^{-1}$

(12) 1-(4-Aminophenyl)-3-(difluoromethyl)-5-[4(methylthio)phenyl]pyrazole.
IR (Film) : 3500, 3380, 1625, 1520 cm$^{-1}$

(13) Ethyl 1-(4-aminophenyl)-5-[4-(methylsulfonyl)phenyl]pyrazole-3-carboxylate.
mp : 245°–247° C.
IR (Nujol) : 3450, 3350, 1740, 1645, 1605, 1520 cm$^{-1}$
NMR (DMSO-d$_6$, δ) : 1.32 (3H, t, J=7Hz), 3.24 (3H, s), 4.33 (2H, q, J=7Hz), 5.51 (2H, s), 6.5–8.0 (9H, m)
Mass (m/z) : 385 (M$^+$)

The following compounds (Examples 35-1) and 35-2)) were obtained according to a similar manner to that of Example 27.

EXAMPLE 35

(1) 5-[4-(Acetamido)phenyl]-1-(4-fluorophenyl)pyrazole-3-carboxamide.
mp 273°–275° C.
IR (Nujol) : 3500, 3200, 1670, 1600, 1550, 1510 cm$^{-1}$
Mass (m/z) : 338 (M$^+$)

(2) 1-[4-(Acetamido)phenyl]-5-[4-(methylsulfonyl)phenyl]pyrazole-3-carbonitrile.
mp : 206°–207° C.
IR (Nujol) : 3270, 2250, 1690, 1670, 1605, 1555, 1515 cm$^{-1}$
NMR (DMSO-d$_6$, δ) : 2.07 (3H, s), 3.25 (3H, s), 7.3–8.0 (9H, m), 10.21 (1H, s)
Mass (m/z) : 380 (M$^+$), 338

The following compound (Example 36) was obtained according to a similar manner to that of Example 29.

EXAMPLE 36

1-[4-(Methylsulfonylamino)phenyl]-5-[4-methylsulfonyl)phenyl]pyrazole-3-carbonitrile.
mp 232°–233° C.
IR (Nujol) : 3240, 2250, 1600, 1515 cm$^{-1}$
NMR (DMSO-d$_6$, δ) : 3.09 (3H, s), 3.26 (3H, s), 7.2–8.0 (9H, m), 10.17 (1H, s)
Mass (m/z) : 416 (M$^+$)

The following compounds (Examples 37-1) to 37-4)) were obtained according to a similar manner to that of Example 31.

EXAMPLE 37

(1) 1-[4-(Dimethylamino)phenyl]-5-[5-(methylsulfonyl)-2-thienyl]pyrazole-3-carbonitrile.
mp : 168°–169° C.
IR (Nujol) : 2250, 1610, 1525 cm$^{-1}$
NMR (DMSO-d$_6$, δ) : 3.01 (6H, s), 3.33 (3H, s), 6.7–7.8 (7H, m)
Mass (m/z) : 372 (M$^+$)

(2) 1-[4-(Ethylamino)phenyl]-5-[4-(methylsulfonyl)phenyl]pyrazole-3-carbonitrile.
mp : 167°–168° C.
IR (Nujol) : 3400, 2240, 1610, 1525 cm$^{-1}$
NMR (CDCl$_3$, δ) : 1.28 (3H, t, J=7Hz), 3.07 (3H, s), 3.13 (2H, q, J=7Hz), 6.5–8.0 (9H, m)
Mass (m/z) : 366 (M$^+$), 351

(3) 1-[4-(Diethylamino)phenyl]-5-[4-(methylsulfonyl)phenyl]pyrazole-3-carbonitrile.
mp : 155°–156° C.
IR (Nujol) : 2240, 1610, 1520 cm$^{-1}$
NMR (CDCl$_3$, δ) : 1.18 (6H, t, J=7Hz), 3.07 (3H, s), 3.37 (4H, q, J=7Hz), 6.5–8.0 (9H, m) .
Mass (m/z) : 394 (M$^+$), 379

(4) 3-(Fluoromethyl)-1-[4-(methylamino)phenyl]-5-[4-(methylsulfonyl)phenyl]pyrazole.
mp : 151°–153° C.
IR (Nujol) : 3425, 1615, 1535 cm$^{-1}$
NMR (CDCl$_3$, δ) 2.85 (3H, s), 3 06 (3H, s), 3.94 (1H, s), 5.36 (1H, s), 5.60 (1H, s), 6.5–8.0 (9H, m)
Mass (m/z) : 359 (M$^+$)

EXAMPLE 38

A mixture of ethyl 1-(4-fluorophenyl)-5-[5-(methylthio)-2-thienyl]pyrazole-3-carboxylate (2.1 g) and sodium methoxide (895 mg) in formamide (10 ml) was stirred at 100° C. for 1 hour. Water was added to the reaction mixture, and the precipitates were collected, washed with water, and dried invacuo to give crystals of 1-(4-fluorophenyl)-5-[5-(methylthio)-2-thienyl]-pyrazole-3-carboxamide (1.6 g).

mp : 132°-140° C.

IR (Nujol) : 3500, 3300, 3200, 1700, 1665, 1600, 1510 cm$^{-1}$

Mass (m/z) : 333 (M+)

The following compounds (Examples 39-1) to 39-16)) were obtained according to a similar manner to that of Example 38.

EXAMPLE 39

(1) 5-[5-(Methylthio)-2-thienyl]-1-(4-nitrophenyl)-pyrazole-3-carboxamide.

IR (Nujol) : 3350, 3180, 1675, 1595, 1520 cm$^{-1}$ (2) 1-(4-Fluorophenyl)-5-[4-(N-formylmethylamino)-phenyl]pyrazole-3-carboxamide.

mp : 222°-224° C.

IR (Nujol) : 3500, 3430, 3200, 1660, 1615, 1510 cm$^{-1}$

Mass (m/z) : 338 (M+)

(3) 5-(4-Aminophenyl)-1-(4-fluorophenyl)pyrazole-3-carboxamide.

mp : 195°-199° C.

IR (Nujol) : 3500, 3360, 3200, 1675, 1630, 1610, 1510 cm$^{-1}$

Mass (m/z) : 296 (M+)

(4) 1-[4-(N-Formylmethylamino)phenyl]-5-(4-tolyl)-pyrazole-3-carboxamide.

mp : 202°-206° C.

IR (Nujol) : 3400, 3200, 1665, 1610, 1520 cm$^{-1}$

Mass (m/z) : 334 (M+)

(5) 1-(4-Fluorophenyl)-5-(4-methoxyphenyl)pyrazole-3-carboxamide.

mp : 136°-142° C.

IR (Nujol) : 3500, 3350, 3200, 1705, 1690, 1665, 1610, 1510 cm$^{-1}$

Mass (m/z) : 311 (M+)

(6) 5-(4-Methoxyphenyl)-1-(4-nitrophenyl)pyrazole-3-carboxamide.

mp : 200°-202° C.

IR (Nujol) : 3400, 3170, 1680, 1610, 1595, 1520 cm$^{-1}$

Mass (m/z) : 338 (M+)

(7) 1,5-Bis(4-methoxyphenyl)pyrazole-3-carboxamide.

mp : 130°-131° C.

IR (Nujol) : 3450, 3300, 3250, 1675, 1660, 1610, 1515 cm$^{-1}$

NMR DMSO-d$_6$, δ) : 3.75 (3H, s), 3.78 (3H, s), 6.7-7.6 (11H, m)

Mass (m/z) : 323 (M+)

(8) 5-(4-Acetylphenyl)-1-(4-fluorophenyl)pyrazole-3-carboxamide.

mp : >300° C.

IR (Nujol) : 3500, 3420, 1675, 1590, 1510 cm$^{-1}$ (9) 5-(4-Cyanophenyl)-1-(4-fluorophenyl)pyrazole-3-carboxamide.

mp : 181°-185° C.

IR (Nujol) : 3500, 3350, 2240, 1660, 1600, 1510 cm$^{-1}$

Mass (m/z) : 306 (M+)

(10) 1-(2-Fluorophenyl)-5-[4-(methylthio)phenyl]-pyrazole-3-carboxamide.

mp : 140°-146° C.

IR (Nujol) : 3400, 3300, 1670, 1600, 1500 cm$^{-1}$

Mass (m/z) : 327 (M+)

(11) 1-(2,5-Difluorophenyl)-5-[4-(methylthio)phenyl]-pyrazole-3-carboxamide.

mp 185°-187° C.

IR (Nujol) : 3450, 3300, 3150, 1690, 1610, 1510 cm$^{-1}$

NMR (DMSO-d$_6$, δ) : 2.46 (3H, s), 7.0-7.8 (10H, m)

Mass (m/z) : 345 (M+)

(12) 1-[4-(N-Formylmethylamino)phenyl]-5-[4-(methylthio)phenyl]pyrazole-3-carboxamide.

mp : 183°-189° C.

IR (Nujol) : 3350, 3200, 1670, 1655, 1605, 1520 cm$^{-1}$

NMR (DMSO-d$_6$, δ) : 2.47 (3H, s), 3.23 (3H, s), 6 9-7.7 (11H, m), 8.65 (1H, s)

Mass (m/z) : 366 (M+)

(13) 5-[4-(Methylthio)phenyl]-1-(2-nitrophenyl)-pyrazole-3-carboxamide.

mp : 196°-199° C. (dec.)

IR (Nujol) : 3500, 3160, 1690, 1610, 1530 cm$^{-1}$

Mass (m/z) : 354 (M+)

(14) 1-(4-Fluoro-2-nitrophenyl)-5-[4-(methylthio)-phenyl]pyrazole-3-carboxamide.

IR (Nujol) : 3430, 3200, 1670, 1590, 1540, 1510 cm$^{-1}$

(15) 1-[4-(N-Formylmethylamino)phenyl]-5-[4-(methylsulfonyl)phenyl]pyrazole-3-carboxamide.

mp : 278°-283° C. (dec.)

IR (Nujol) : 3350, 1665, 1600, 1520 cm$^{-1}$

Mass (m/z) : 398 (M+)

(16) 1-(2-Chlorophenyl)-5-[4-(methylthio)phenyl]-pyrazole-3-carboxamide.

mp : 195°-201° C.

IR (Nujol) : 3450, 3150, 1690, 1610, 1590 cm$^{-1}$

Mass (m/z) : 343 (M+)

EXAMPLE 40

A mixture of 1-(4-aminophenyl)-5-[5-(methylsulfonyl)-2-thienyl]pyrazole-3-carbonitrile (1.1 g) and formic acid (5 ml) was refluxed for 30 minutes. The mixture was concentrated and the residue was triturated in water to give crystals of 1-[4-(formylamino)phenyl]-5-[5-(methylsulfonyl)-2-thienyl]pyrazole-3-carbonitrile (1.1 g).

mp : 152°-158° C.

IR (Nujol) : 3260, 2250, 1675, 1605, 1515 cm$^{-1}$

Mass (m/z) : 372 (M+)

The following compounds (Examples 41-1) to 41-11)) were obtained according to a similar manner to that of Example 40.

EXAMPLE 41

(1) Ethyl 1-[4-(formylamino)phenyl]-5-(4-tolyl)-pyrazole-3-carboxylate.

mp : 201°-203° C.

IR (Nujol) : 3260, 1730, 1690, 1600, 1530 cm$^{-1}$ (2) 1-[4-(Formylamino)phenyl]-5-(4-methoxyphenyl)-pyrazole-3-carbonitrile.

IR (Film) : 3300, 2250, 1690, 1610, 1515 cm$^{-1}$ (3) Ethyl 1-[4-(formylamino)phenyl]-5-[4-(methylthio)-phenyl]pyrazole-3-carboxylate.

mp : 190°-192° C.

IR (Nujol) : 3250, 1730, 1690, 1605, 1520 cm$^{-1}$ (4) 1-[4-(Formylamino)phenyl]-5-[4-(methylsulfonyl)-phenyl]pyrazole-3-carbonitrile.

mp : 195°-197° C.

IR (Nujol) : 3270, 2240, 1690, 1670, 1605, 1550, 1515 cm$^{-1}$

NMR (DMSO-d$_6$, δ) : 3.26 (3H, s), 7.2-8.0 (9H, m), 8.32 (1H, s), 10.48 (1H, s)

Mass (m/z) : 366 (M+)

(5) 1-[2-(Formylamino)phenyl]-5-[4-(methylsulfonyl)-phenyl]pyrazole-3-carbonitrile.

mp : 109°-118° C.

IR (Nujol) : 3330, 2250, 1700, 1600, 1520 cm⁻¹
Mass (m/z) : 366 (M⁺), 338

(6) 1-[4-(Formylamino)phenyl]-5-[4-(methylthio)phenyl]-3-(trifluoromethyl)pyrazole.
mp : 134°-135° C.
IR (Nujol) : 3370, 1700, 1605, 1530 cm⁻¹
Mass (m/z) : 377 (M⁺)

(7) 1-[4-(Formylamino)phenyl]-5-[4-(methylsulfonyl)phenyl]-3-(trifluoromethyl)pyrazole..
mp : 163°-166° C.
IR (Nujol) : 3270, 1680, 1610, 1550, 1520, 1500 cm⁻¹
Mass (m/z) : 409 (M⁺)

(8) 1-[4-(Formylamino)phenyl]-5-[4-(methylsulfinyl)phenyl]-3-(trifluoromethyl)pyrazole.
IR (Film) : 3270, 1690, 1610, 1525, 1500 cm⁻¹

(9) 1-[4-(Formylamino)phenyl]-3-(methylsulfonyl)-5-[4-methylsulfonyl)phenyl]pyrazole.
mp 193°-195° C.
IR (Nujol) : 3380, 1700, 1670, 1605, 1535 cm⁻¹
Mass (m/z) : 419 (M⁺)

(10) 3-(Difluoromethyl)-1-[4-(formylamino)phenyl]-5-[4-(methylthio)phenyl]pyrazole.
mp : 127°-131° C.
IR (Nujol) : 3300, 1680, 1670, 1610, 1520 cm⁻¹
Mass (m/z) : 359 (M⁺)

(11) Ethyl 1-[4-(formylamino)phenyl]-5-[4-(methylsulfonyl)phenyl]pyrazole-3-carboxylate.
mp : 214°-216° C.
IR (Nujol) : 3270, 1740, 1670, 1605, 1555, 1510 cm⁻¹
Mass (m/z) : 413 (M⁺)

EXAMPLE 42

A solution of 1-[4-(formylamino)phenyl]-5-[5-(methylsulfonyl)-2-thienyl]pyrazole-3-carbonitrile (1.1 g) in N,N-dimethylformamide (3 ml) was added dropwise to a suspension of sodium hydride (60%; 118 mg) in N,N-dimethylformamide (2 ml). The mixture was stirred at 0° C. for 30 minutes. To the mixture was added dropwise a solution of iodomethane (0.84 g) in N,N-dimethylformamide (2 ml) at 0° C. The resulting mixture was stirred at 0° C. for 1 hour, poured into an ice-cooled dilute hydrochloric acid, and extracted with ethyl acetate. The extract was washed with water, dried over magnesium sulfate, and evaporated in vacuo. The residue was recrystallized from ethanol to give crystals of 1-[4-(N-formylmethylamino)phenyl]-5-[5-(methylsulfonyl)-2-thienyl]pyrazole -3-carbonitrile (1 g).
mp : 170°-173° C.
IR (Nujol) : 2250, 1675, 1600, 1520 cm⁻¹
Mass (m/z) : 386 (M⁺)

The following compounds (Examples 43-1) to 43-12)) were obtained according to a similar manner to that of Example 42.

EXAMPLE 43

(1) Ethyl 1-(4-fluorophenyl)-5-[4-(N-formylmethylamino)phenyl]pyrazole-3-carboxylate.
mp : 118°-120° C.
IR (Nujol) : 1715, 1680, 1610, 1515 cm⁻¹
NMR (CDCl₃, δ) : 1.43 (3H, t, J=7Hz), 3.32 (3H, s), 4.46 (2H, q, J=7Hz), 7.0-7.05 (9H, m), 8.55 (1H, s)
Mass (m/z) : 367 (M⁺)

(2) Ethyl 1-[4-(N-formylmethylamino)phenyl]-5-(4-tolyl)pyrazole-3-carboxylate.
IR (Film) : 1720, 1675, 1610, 1515 cm⁻¹
NMR (CDCl₃, δ) : 1.39 (3H, t, J=7Hz), 2.32 (3H, s), 3.28 (3H, s), 4.42 (2H, q, J=7Hz), 6.9-7.5 (9H, m), 8.42 (1H, s)

(3) 1-[4-(N-Formylmethylamino)phenyl]-5-(4-methoxyphenyl)pyrazole-3-carbonitrile.
IR (Film) : 2250, 1680, 1610, 1515 cm⁻¹

(4) Ethyl 1-[4-(N-formylmethylamino)phenyl]-5-[4-(methylthio)phenyl]pyrazole-3-carboxylate.
IR (Film) : 1720, 1680, 1605, 1520 cm⁻¹
NMR (CDCl₃, δ) : 1.42 (3H, t, J=7Hz), 2.47 (3H, s), 3.28 (3H, s), 4.42 (2H, q, J=7Hz), 6.9-7.4 (9H, m), 8.37 (1H, s)

(5) 1-[4-(N-Formylmethylamino)phenyl]-5-[4-(methylsulfonyl)phenyl]pyrazole-3-carbonitrile.
Mass (m/z) : 380 (M⁺)

(6) 1-[2-(N-Formylmethylamino)phenyl]-5-[4-(methylsulfonyl)phenyl]pyrazole-3-carbonitrile.
mp : 172°-173° C.
IR (Nujol) : 2250, 1670, 1600, 1500 cm⁻¹
Mass (m/z) : 380 (M⁺), 352

(7) 1-[4-(N-Formylmethylamino)phenyl]-5-[4-(methylthio)phenyl]-3-(trifluoromethyl)pyrazole.
mp : 142°-144° C.
IR (Nujol) : 1680, 1610, 1520, 1500 cm⁻¹
Mass (m/z) : 391

(8) 1-[4-(N-Formylmethylamino)phenyl]-5-[4-(methylsulfonyl)phenyl]-3-(trifluoromethyl)pyrazole.
mp : 118°-120° C.
IR (Nujol) : 1660, 1610, 1520, 1500 cm⁻¹
Mass (m/z) : 423 (M⁺)

1-[4-{N-Formylmethylamino)phenyl]-5-[4-(methylsulfinyl)phenyl-3-(trifluoromethyl)pyrazole.
IR (Film) : 1675, 1610, 1520, 1500 cm⁻¹

(10) 1-[4-(N-Formylmethylamino)phenyl]-3-(methylsulfonyl)-5-[4-(methylsulfonyl)phenyl]pyrazole.
mp : 146°-150° C.
IR (Nojol) : 1675, 1605, 1520 cm⁻¹
Mass (m/z) : 433 (M⁺)

(11) 3-(Difluoromethyl)-1-[4-formylmethylaminophenyl]-5-[4-methylthio)phenyl]pyrazole.
mp : 109°-115° C.
IR (Nujol): 1680, 1605, 1520 cm⁻¹
Mass (m/z) : 373 (M⁺)

(12) Ethyl 1-[4-N-formylmethylamino)phenyl]-5-[4-(methylsulfonyl)phenyl]pyrazole-3-carboxylate
IR (Nujol) : 1745, 1725, 1680, 1600, 1520 cm⁻¹
Mass (m/z) : 427 (M⁺)

EXAMPLE 14

A mixture of 1-[4-(N-formylmethylamino)phenyl]-5-[5-(methylsulfonyl)-2-thienyl]pyrazole-3-carbonitrile (methylsulfonyl)-2-thienyl]pyrazole-3-carbonitrile (1 g) and 10% hydrochloric acid (3 ml) in methanol (15 ml) was stirred at 60° C. for 3 hours. After cooled, the mixture was filtered and the filtrate was concentrated in vacuo. The residue was washed with ethanol to give crystals of 1-[4-(methylamino)phenyl]-5-[5-methylsulfonyl)-2-thienyl]pyrazole-3-carbonitrile hydrochloride (0.89 g).
mp: 205°-207° C.
IR (Nujol): 2600, 2450, 2250, 1510 cm⁻¹
NMR (DMSO-d₆, δ): 2.76 (3H, s), 6.77 (2H, d, J=8Hz), 7.26 (2H, d, J=8Hz), 7.43 (1H, d, J=3Hz), 7.72 (1H, s), 7.78 (1H, d, J=3Hz)
Mass (m/z): 358 (M⁺)

The following compounds (Examples 45-1) to 45-14)) were obtained according to a similar manner to that of Example 44.

EXAMPLE 45

1) 1-(4-Fluorophenyl)-5-(methylamino)phenyl]pyrazole-3-carbonitrile hydrochloride.
mp: 189°-191° C.
IR (Nujol): 2650, 2450, 2250, 1510 cm⁻¹

NMR (DMSO-d$_6$, δ): 2.73 (3H, s), 6.8-7.5 ( (9H, m)
Mass (m/z): 292 (M+)

2) 1-[4-Methylamino)phenyl]-5-(4-tolyl)pyrazole-3-carbonitrile hydrochloride.
mp: 199°-201° C.
IR (Nujol): 2600, 2450, 2250, 1610, 1520 cm$^{-1}$
NMR (DMSO-d$_6$, δ): 2.29 (3H, s), 2.76 (3H, s), 6.9-7.4 (9H, m), 7.62 (2H, s) Mass (m/z): 288 (M+)

3) 1-[4-(Methylamino)phenyl]-5-[4-(methylsulfonyl)-phenyl]pyrazole-3-carbonitrile hydrochloride.
mp: 218°-221° C.
IR (Nujol): 3450, 2650, 2460, 2250, 1600, 1510 cm$^{-1}$
NMR (DMSO-d$_6$, δ): 2.70 (3H, s), 3.25 (3H, s), 5.46 (2H, s), 6.5-8.0 (9H, m)
Mass (m/z): 352 (M+)

4) 1-[4-Methylamino)phenyl]-5-[4-(methylthio)phenyl]-pyrazole-3-carbonitrile hydrochloride.
mp: 113°-120° C.
IR (Nujol): 3400, 2650, 2450, 2250, 1600, 1515 cm$^{-1}$
NMR (DMSO-d$_6$, δ): 2.46 (3H, s), 2.74 (3H, s), 6.57 (2H, s), 6.5-7.4 (9H, m)
Mass (m/z): 320 (M+)

5) 1-[4-(Methylamino)phenyl]-5-[4-1-(methylsulfinul)-phenyl]pyrazole-3-carbonitrile hydrochloride.
mp: 175°-177° C. (dec.)
IR (Nujol): 2630, 2450, 2250, 1600, 1515 cm$^{-1}$
NMR (DMSO-d$_6$, δ): 2.74 (3H, s), 2.76 (3H, s), 6.53 (2H, s), 6.7-7.8 (9H, m)
Mass (m/z): 336 (M+), 319 6) 1-[2-(Methylamino)-phenyl]-5-[4-(methylsulfonyl)-phenyl]pyrazole-3-carbonitrile.
mp: 192°-193° C.
IR (Nujol): 3450, 2250, 1610, 1520
NMR (DMSO-d$_6$, δ(: 2.66 (3H, d, J=5Hz), 3.22 (3H, s), 5.33 (1H, q, J=5Hz), 6.5-8.0 (9H, m)
Mass (m/z): 352 (M+)

7) 1-[4-(Methylamino)phenyl]-5-[4-(methylthio)-phenyl]-3-(trifluoromethyl)pyrazole.
mp: 168°-169° C.
IR (Nujol): 3400, 1610, 1535, 1500 cm$^{-1}$
NMR (CDCl$_3$, δ): 2.47 (3H, s), 2.84 (3H, s), 6.5-7.3 (9H, m)
Mass (m/z): 363 (M+)

8) 1-[4-(Methylamino)phenyl]-5-[4-(methylsulfonyl)-phenyl]-3-(trifluoromethyl)pyrazole hydrochloride.
mp: 200°-202° C.
IR (Nujol): 2725, 2600, 2450, 1600, 1520, 1500 cm$^-$
NMR (DMSO-d$_6$, δ): 2.75 (3H, s), 3.26 (3H, s), 6.8-8.0 (9H, m), 8.42 (2H, s)
Mass (m/z): 395 (M+)

9) 1-[4-(Methylamino)phenyl]-5-[4-(methylsulfinyl)-phenyl]3-(trifluoromethyl)pyrazole hydrochloride.
mp: 171°-172° C.
IR (Nujol): 2625, 2450, 1500 cm$^{-1}$
NMR (DMSO-d$_6$, δ): 2.76 (6H, s), 6.8-7.8 (10H, m)
Mass (m/z): 379 (M+)

10) 1-[4-(Methylamino)phenyl]-3-(methylsulfonyl)-5-[4-(methylsulfonyl)phenyl]pyrazole hydrochloride.
mp: 209°-211° C.
IR (Nujol): 2650, 2450, 1600, 1515 cm$^{-1}$
NMR (DMSO-d$_6$, δ): 2.74 (3H, s), 3.26 (3H, s), 3.35 (3H, s), 6.7-8.0 (9H, m)
Mass (m/z): 405 (M+)

11) 3-(Difluoromethyl)-1-[4-(methylamino)phenyl]-5-[4-(methylthio)phenyl]pyrazole
mp: 128°-129° C.
IR (Nujol): 3360. 1610, 1530 cm$^{-1}$
NMR (DMSO-d$_6$, δ): 2.47 (3H, s), 2.84 (3H, s), 6.4-7.2 (10H, m)
Mass (m/z): 345 (M+)

12) N-Methyl-1-[4-(methylamino)phenyl]-5-[4-methylsulfonyl)phenyl]pyrazole-3-carboxamide.
mp: 187°-188° C.
IR (Nujol): 3400, 1670, 1650, 1610, 1560, 1525 cm$^{-1}$
NMR (CDCl$_3$, δ): 2.86 (3H, s), 2.92 (3H, d, J=5Hz), 3.06 (3H, s), 4.03 (1H, s), 6.5-8.0 (10H, m)
Mass (m/z): 3.84 (M+)

13) N,N-Dimethyl-1-[4-(methylamino)phenyl]-5-[4-(methylsulfonyl)phenyl]pyrazole-3-carboxamide.
mp: 204°-205° C.
IR (Nujol): 3420, 1620, 1530 cm$^-$
NMR (CDCl$_3$, δ): 2.86 (3H, s), 3.07 (3H, s), 3.14 (3H, s), 3.44 (3H, s), 4.00 (1H, s), 6.4-8.0 (9H, m)
Mass (m/z): 398 (M+)

14) 1-[4-(Methylamino)phenyl]-5-[4-(methylsulfonyl)-phenyl]pyrazole-3-carboxamide
mp: 215°-216° C.
IR (Nujol): 3470, 3370, 3160, 1675, 1610, 1530 cm$^-$
NMR (CDCl$_3$, δ): 2.69 (3H, d, J=5Hz), 3.24 (3H, s), 6.07 (1H, q, J=5Hz), 6.55 (2H, d, J=9Hz), 7.0-8.0 (9H, m)
Mass (m/z): 370 (M+)

EXAMPLE 46

Ethyl 1-[4-(methylamino)phenyl]-5-[4-(methylsulfonyl)phenyl]pyrazole-3-carboxylate, which was obtained according to a similar manner to that of Example 44, was reacting according to a similar manner to that of Example 3 to give 1-[4-(methylamino)phenyl]-5-[4-(methysulfonyl)-phenyl]pyrazole-3-carboxylic acid.
mp: 235°-240° C. (dec.)
IR (Nujol): 3400, 1715, 1610, 1530 cm $^{-1}$
NMR (DMSO-d$_6$, δ): 2.69 (3H, s), 3.24 (3H, s), 6.09 (1H, s), 6.55 (2H, d, J=9Hz), 7.05 (2H, d, J=9Hz), 7.17 (1H, s), 7.53 (2H, d, J=8Hz), 7.89 (2H, d, J=8Hz)
Mass (m/z): 371 (M+)

EXAMPLE 47

A mixture of 1-(4-fluoropheny)-5-[4-(methylsulfonyl)phenyl]pyrazole-3-carbonitrile (1 g), ammonium chloride (0.25 g) and sodium azide (0.24 g) in N,N-dimethylformamide (10 ml) was stirred at 105° C. for 10 hours. The mixture was poured into ice-water, and the precipitates were collected, washed with water, and recrystallized from a mixture of ethanol and tetrahydrofuran to give crystals of 1-(4-fluorophenyl)-5-[4-(methylsulfonyl)phenyl]-3-(5-tetrazolyl)pyrazole (0.71 g).
mp: 278°-279° C. (dec.)
IR (Nujol): 3150, 1655, 1620, 1600, 1510 cm$^{-1}$
NMR (DMSO-d$_6$, δ): 3.27 (3H, s), 7.3-7.6 (7H, m), 7.95 (2H, d, J=8Hz)
Mass (m/z): 384 (M+)

The following compounds (Examples 48-1) and 48-2)) were obtained according to a similar manner to that of Example 47.

EXAMPLE 48

1) 1-(4-Fluorophenyl)-5-[4-(methylthio)phenyl]-3-(5-tetrazolyl)pyrazole.
mp: 242°-243° C. (dec.)
IR (Nujol): 1605, 1510 cm$^-$
NMR (CDCl$_3$, δ): 2.48 (3H, s), 7.1-7.6 (9H, s)
Mass (m/z): 352 (M+)

2) 1-(4-Fluorophenyl)-5-[4-(methylsulfinyl)phenyl]-3-(5-tetrazolyl)pyrazole.
mp: 272°-273° C. (dec.)
IR (Nujol): 1615, 1510 cm⁻
NMR (CDCl₃, δ): 2.79 (3H, s), 7.3-7.8 (9H, m)
Mass (m/z): 368 (M+)

EXAMPLE 49

A mixture of ethyl 4-[4-(formylamino)phenyl]-2,4-dioxobutanoate (6 g) and 4-fluorophenylhydrazine hydrochloride (4.1 g) in acetic acid (30 ml) was stirred at 100° C. for 2 hours. The mixture was concentrated, and the residue was treated with 10% hydrochloric acid (10 ml) and methanol (40 ml) at 60° C. for 2 hours. The solvent was evaporated, and the residue was dissolved in water. The obtained solution was neutralized and extracted with ethyl acetate. The extract was washed with water, dried, and concentrated in vacuo. The residue was washed with ethanol to give crystals of ethyl 5-(4-aminophenyl)-1-(4-fluorophenyl)pyrazole-3-carboxylate (3.4 g).
mp: 158°-160° C.
IR (Nujol): 3450, 3350, 3250, 1720, 1640, 1610, 1510 cm⁻¹
NMR (CDCl₃, δ): 1.42 (3H, t, J=7Hz), 4.44 (2H, q, J=7Hz), 6.5-7.4 (9H, m)
Mass (m/z): 325 (M+)

EXAMPLE 50

A solution of sodium nitrite (0.26 g) in water (0.3 ml) was added to an ice-salt cooled mixture of 1-(4-fluorophenyl)-5-[4-(methylthio)phenyl]-3-pyrazolamine (1 g), acetonitrile (1 ml), sulfuric acid (0.6 ml) and water (1.6 ml). The mixture was stirred at 0° C. for 30 minutes. The resulting mixture was added portionwise to a mixture of cuprous bromide (645 mg), sodium bromide (582 mg), hydrobromic acid (1.7 ml) and water (3 ml) at 80° C. The mixture was stirred at 80° C. for 30 minutes and extracted with toluene. The extract was washed with water, dried, and evaporated in vacuo. The obtained residue was purified by column chromatography on silica gel (10 g) to give crystals of 3-bromo-1-(4-fluorophenyl)-5-[4-(methylthio)phenyl]pyrazole (0.35 g).
mp: 98°-99° C.
IR (Nujol): 1600, 1510, 1680 cm⁻
NMR (CDCl₃, δ): 2.48 (3H, s), 6.49 (1H, s), 6.9-7.3 (8H, m)
Mass (m/z): 364 (M+)

EXAMPLE 51

A mixture of 4-bromo-1-(4-fluorophenyl)-5-[4-(methylthio)phenyl]pyrazole (1.9 g) and cuprous cyanide (0.7 g) was heated at 200° C. for 6 hours. The mixture was extracted with ethyl acetate and the extract was concentrated in vacuo. The residue (0.95 g) was purified by column chromatography on silica gel (20 g) eluting with chloroform to give crystals of 1-(4-fluorophenyl)-5-[4-(methylthio)phenyl]pyrazole-4-carbonitrile (0.95 g).
mp: 122°-123° C.
IR (Nujol): 2230, 1600, 1505 cm⁻¹
NMR (CDCl₃, δ): 2.50 (3H, s), 7.0-7.8 (8H, m), 8.00 (1H, s)
Mass (m/z): 309 (M+)

EXAMPLE 52

A solution of bromine (0.9 g) in dichloromethane (2 ml) was added dropwise to an ice-cooled solution of 1-(4-fluorophenyl)-5-[4-(methylthio)phenyl]pyrazole (1.6 g) in dichloromethane (10 ml). The mixture was stirred at 5° C. for 1 hour, washed with a solution of sodium bisulfite and water, dried, and concentrated in vacuo. The residue (1.9 g) was recrystallized from ethanol to give crystals of 4-bromo-1-(4-fluorophenyl)-5-[4-(methylthio)phenyl]pyrazole (1.3 g).
mp: 85°-87° C.
IR (Nujol): 1600, 1510 cm⁻¹
Mass (m/z): 364, 362

EXAMPLE 53

A mixture of 1-[4-(methylthio)phenyl]-3,3-bis-(methylthio)-2-propen-1-one (2.7 g) and 4-fluorophenylhydrazine hydrate (1.8 g) in acetic acid (15 ml) was stirred at 100° C. for 7 hours. The solvent was evaporated and the residue was dissolved in ethanol. The insoluble material was filtered and the filtrate was concentrated in vacuo. The residue was purified by column chromatography on silica gel (25 g) eluting with chloroform to give an oil of 1-(4-fluorophenyl)-3-(methylthio)-5-[4-(methylthio)phenyl]pyrazole (0.73 g).
IR (Nujol): 1590, 1510 cm⁻¹
NMR (CDCl₃, δ): 2.48 (3H, s), 2.59 (3H, s), 6.40 (1H, s), 6.9-7.4 (8H, m)

The following compound (Example 54) was obtained according to a similar manner to that of Example 53.

EXAMPLE 54

3-(Methylthio)-5-[4-(methylthio)phenyl]-1-(4-nitrophenyl)pyrazole.
mp: 71°-73° C.
IR (Nujol): 1595, 1515, 1500 cm⁻
Mass (m/z): 357 (M+)

EXAMPLE 55

A mixture of 5-(4-aminophenyl)-1-(4-fluorophenyl)-pyrazole-3-carboxamide (0.27 g) and methanesulfonyl chloride (0.63 g) in pyridine (5 ml) was stirred at 60° C. for 5 hours. The solvent was evaporated and the residue was dissolved in a mixture of ethyl acetate and water. The organic layer was separated, washed with water, dried, and concentrated in vacuo. The residue was crystallized from ethanol to give 1-(4-fluorophenyl)-5-[4-methylsulfonylamino)phenyl]pyrazole-3-carbonitrile (0.19 g).
mp: 202°-205° C.
IR (Nujol): 3160, 2250, 1615, 1510 cm⁻
(DMSO-d₆, δ): 3.05 (3H, s), 7.1-7.5 (9H, m), 10.06 (1H, s)
Mass (m/z): 356 (M+), 277

EXAMPLE 56

A mixture of 1-(2-amino-4-fluorophenyl)-5-[4-(methylsulfonyl)phenyl]pyrazole-3-carbonitrile (0.87 g), methyl iodide (pb 0.69 g), and potassium carbonate (0.27 g) in N,N-dimethylformamide (b 5 ml) was stirred at 45° C. for 19 hours. The mixture was poured into water and extracted with ethyl acetate. The extract was washed with water, dried, and concentrated in vacuo. The residue (1 g) was purified by column chromatography on silica gel (15 g) eluting with chloroform.

1-['-(Dimethylamino)-4-fluorophenyl]-5-[4-(methylsulfonyl)phenyl]pyrazole-3-carbonitrile (0.11 g) was obtained from the first eluate.
mp: 200°-202° C.
IR (Nujol): 2250, 1620, 1500 cm⁻

NMR (DMSO-d6, δ): 2.11 (6H, s), 3.21 (3H, s), 6.7-7.9 (8H, m)

Mass (m/z): 384 (M+)

1-[4-Fluoro-2-(methylamino)phenyl-5-[4-(methylsulfonyl)phenyl]pyrazole-3-carbonitrile (0.44 g) was obtained from the second eluate.

mp: 192°-193° C.

IR (Nujol): 3450, 2250, 1620, 1530 cm⁻

NMR (DMSO-d6, δ): 2.65 (3H, d, J=3Hz), 3.23 (3H, s), 5.68 (1H, q, J=3Hz), 6.3-8.0 (8H, m)

Mass (m/z): 370 (M+)

EXAMPLE 57

A mixture of 1-(4-fluorophenyl-3-(methylthio)-5-[4-(methylthio)phenyl]pyrazole (0.73 g), 30% hydrogen peroxide (1.5 ml) and conc. sulfuric acid (2 drops) in acetic acid (10 ml) was stirred at 60° C. for 4 hours. The solvent was evaporated and the residue was dissolved in ethyl acetate. The solution was washed successively with an aqueous solution of sodium bicarbonate and water, dried, and concentrated. The residue was recrystallized from a mixture of ethyl acetate and ethanol to give crystals of 1-(4-fluorophenyl)-3-(methylsulfonyl)-5-[4-(methylsulfonyl)phenyl]pyrazole (0.54 g).

mp: 209°-210° C.

IR (Nujol): 1600, 1515 cm⁻

NMR (DMSO-d6, δ): 3.26 (3H, s), 3.38 (3H, s),

Mass (m/z): 394 (M+)

The following compound (Example 58) was obtained according to a similar manner to that of Example 57.

EXAMPLE 58

3-(methylsulfonyl)-5-[4-(methylsulfonyl)phenyl]-1-(4-nitrophenyl)pyrazole.

mp: 187°-189° C.

IR (Nujol): 1600, 1530, 1500 cm⁻

Mass (m/z): 421

EXAMPLE 59

A mixture of 4-fluoro-1-[4-(methylthio)phenyl]butan-1,3-dione (2 g) and 4-fluorophenylhydrazine hydrochloride (1.6 g) in acetic acid (10 ml) was refluxed for 5 hours. The solvent was evaporated and the residue was dissolved in ethyl acetate. The resulting solution was washed with an aqueous solution of sodium bicarbonate, dried, and concentrated in vacuo. The residue (3 g) was purified by column chromatography on silica gel eluting with chloroform. An oil of 3-(chloromethyl)-1-(4-fluorophenyl) -5-[4-(methylthio)phenyl]pyrazole (1.3 g) was obtained from the first eluate.

IR (Film): 1600, 1510 cm⁻

NMR (CDCl3, δ): 2.44 (3H, s), 4.64 (2H, s), 6.49 (1H, s), 6.8-7.3 (8H, m)

Mass (m/z): 332 (M+)

An oil of 1-(4-fluorophenyl)-5-[4-(methylthio)phenyl]-3-pyrazolylmethyl acetate (0.6 g) was obtained from the second eluate.

IR (Film): 1740, 1600, 1515 cm⁻

NMR (CDCl3, δ): 2.11 (3H, s), 2.44 (3H, s), 5.14 (2H, s), 6.46 (1H, s), 6.8-7.3 (8H, m)

Example 60 m-chloroperbenzoic acid (2.8 g) in dichloromethane (50 ml) was stirred at room temperature overnight. The mixture was washed with a solution of sodium bicarbonate and concentrated in vacuo. To the residual powder (2.1 g) containing N-{1-(4-fluorophenyl)-5-[4-(methylsulfonyl)phenyl]-pyrazol-3-ylmethyl}acetamide was added ethanol (40 ml) and conc. hydrochloric acid (15 ml). The mixture was refluxed for 7 hours and concentrated to dryness. The residue was dissolved in water, then the solution was made basic with sodium hydroxide and extracted with ethyl acetate. The extract was washed with water, dried, and concentrated in vacuo. The obtained residue (1.4 g) was purified by column chromatography on silica gel (100 g) eluting with a mixture of chloroform and methanol (10:1) to give crystals of 1-(4-fluorophenyl)-5-[4-(methylsulfonyl)phenyl]-pyrazol-3-ylmethylamine (1.0 g).

mp 150°-152° C.

IR (Nujol) : 3380, 3300, 1600, 1510 cm⁻¹

NMR (CDCl3, δ) : 1.85 (2H, s), 3.07 (3H, s), 3.99 (2H, s), 6.57 (1H, s), 7.0-7.5 (6H, m), 7.87 (2H, d, J=8Hz)

Mass (m/z) : 345 (M+)

What we claim is:

1. A compound of the formula:

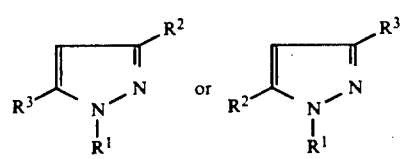

wherein

R¹ is aryl which may be substituted with substituent(s) selected from the group consisting of lower alkyl, halogen, lower alkoxy, lower alkylthio, lower alkylsulfinyl, lower alkylsulfonyl, hydroxy, lower alkylsulfonyloxy, nitro, amino, lower alkylamino, acylamino and lower alkyl(acyl)amino; or a pyridyl group;

R² is methyl substituted with amino, lower alkylamino, halogen or acyloxy; acyl; cyano; halogen; lower alkylthio; lower alkylsulfinyl; or a tetrazolyl group; and R³ is aryl substituted with lower alkyl, lower alkylthio, lower alkylsulfinyl, halogen, amino, lower alkylamino, acylamino, lower alkyl(acyl)amino, lower alkoxy, cyano, hydroxy or acyl; or a thienyl group which may be substituted with lower alkylthio, lower alkysulfinyl or lower alkylsulfonyl;

provided that when R² is carboxy, esterified carboxy or tri(halo)methyl, then R³ is aryl substituted with lower alkylthio, lower alkylsulfinyl, amino, lower alkylamino, acylamino, lower alkyl(acyl)amino, hydroxy or acyl; or a thienyl group substituted with lower alkylthio, lower alkylsulfinyl or lower alkylsulfonyl, or R¹ is aryl substituted with substituent(s) selected from the group consisting of lower alkylthio, lower alkylsulfinyl, lower alkylsulfonyl, hydroxy, lower alkylsulfonyloxy, nitro, amino, lower alkylamino, acylamino and lower alkyl(acyl)amino; or a pyridyl group or pharmaceutically acceptable salt thereof.

2. A compound according to claim 1, wherein $R^2$ is methyl substituted with amino, lower alkylamino or acyloxy; carbamoyl optionally substituted with substituent(s) selected from the group consisting of lower alkyl, cyclo(lower)alkyl, aryl and hydroxy; lower alkanoyl optionally substituted with lower alkoxy; pyrrolidinylcarbonyl; n-methylpiperazinylcarbonyl; cyano; halogen; lower alkylthio; lower alkylsulfinyl; lower alkylsulfonyl; or tetrazolyl.

3. A compound according to claim 2, wherein $R^3$ is aryl or thienyl, each of which is substituted with lower alkylthio, lower alkylsulfinyl, or lower alkylsulfonyl.

4. A compound according to claim 3, wherein
$R^3$ is aryl substituted with lower alkylthio, lower alkylsulfinyl, or lower alkylsulfonyl.

5. A compound according to claim 4, wherein
$R^1$ is phenyl substituted with halogen,
$R^2$ is cyano and $R^3$ is phenyl substituted with lower alkylthio, lower alkylsulfinyl or lower alkylsulfonyl.

6. A compound of claim 5, which is 1-(4-fluorophenyl)-5-[4-(methylsulfonyl)phenyl]pyrazole-3-carbonitrile.

7. A compound of claim 5, which is 1-(4-fluorophenyl)-5-[4-methylsulfinyl)phenyl]pyrazole-3-carbonitrile.

8. A pharmaceutical composition comprising a compound of claim 1, as an active ingredient, in association with a pharmaceutically acceptable, substantially non-toxic carrier or excipient.

9. A method for therapeutic treatment of inflammation pain thrombois and rheumatism which comprises administering an effective amount of a compound of claim 1.

* * * * *